US006939681B1

(12) United States Patent \
Ipsen et al.

(10) Patent No.: US 6,939,681 B1 \
(45) Date of Patent: Sep. 6, 2005

(54) METHOD OF DETECTING AN ANTIBODY IN A LIQUID SAMPLE

(75) Inventors: Hans-Henrik Ipsen, Hillerod (DK); Niels Johansen, Allerod (DK); Rikke Morkeberg, Nærum (DK); Soren Bogestrand, Kokkedal (DK); Tine Charlotte Beck, Birkerod (DK)

(73) Assignee: Alk-Abello A/S, Horsholm (DK)

( * ) Notice: Subject to any disclaimer, the term of this patent is extended or adjusted under 35 U.S.C. 154(b) by 500 days.

(21) Appl. No.: 10/085,768

(22) Filed: Feb. 28, 2002

Related U.S. Application Data

(62) Division of application No. 09/339,545, filed on Jun. 24, 1999, now Pat. No. 6,379,909.

(60) Provisional application No. 60/090,895, filed on Jun. 25, 1998.

(30) Foreign Application Priority Data

Jun. 24, 1998 (DK) ............................... 1998 00821

(51) Int. Cl.$^7$ ..................... G01N 33/53; G01N 33/543; G01N 33/536; C12Q 1/00; C12N 11/00

(52) U.S. Cl. ...................... 435/7.92; 435/4; 435/7.1; 435/7.5; 435/7.9; 435/7.93; 435/7.94; 435/7.95; 435/174; 435/175; 435/176; 435/177; 435/178; 435/179; 435/180; 435/181; 435/182; 435/183; 436/501; 436/512; 436/513; 436/517; 436/518; 436/523; 436/524; 436/525; 436/528; 436/534; 436/536; 436/538; 436/540; 436/542; 436/804; 436/824; 436/825; 436/164; 324/214

(58) Field of Search ..................... 435/4, 7.1, 7.5, 435/7.9, 7.92–7.95, 174–183; 436/501, 512, 436/513, 517, 518, 523, 524, 525, 528, 534, 436/536, 538, 540, 542, 804, 824, 825, 164; 324/214; 424/9.81, 805, 809; 530/862, 866

(56) References Cited

U.S. PATENT DOCUMENTS 4,891,313 A * 1/1990 Berger et al. .............. 435/7.94 \
6,087,188 A * 7/2000 Johansen et al. ........... 436/526

FOREIGN PATENT DOCUMENTS

WO     WO 98/16829 A1 * 4/1998

* cited by examiner

*Primary Examiner*—Chris Chin \
*Assistant Examiner*—Kartic Padmanabhan \
(74) *Attorney, Agent, or Firm*—Watov & Kipnes, P.C.

(57) ABSTRACT

The invention relates to a method of evaluating the immunological status of a subject comprising the steps of 1) determining the content of an antibody in a liquid sample from the subject using an immunoassay, wherein the reaction between the antibody of the sample and a ligand in the form of an antigen, an antibody or a hapten, the ligand being directed to the Fab region of the sample antibody, is carried out in the presence of other constituents of the sample to obtain a measurement 1, 2) determining the content of an antibody in the liquid sample using an immunoassay, wherein the reaction between the antibody of the sample and a ligand in the form of an antigen, an antibody or a hapten, the ligand being directed to the Fab region of the sample antibody, is carried out in the absence of other constituents of the sample to obtain a measurement 2, and 3) interrelating measurements 1 and 2 to express the interference and using the interference as a parameter for evaluating the immunological status of the subject.

17 Claims, 27 Drawing Sheets

METHOD OF DETECTING AN ANTIBODY IN A LIQUID SAMPLE

The present application is a divisional application of U.S. Ser. No. 09/339,545 filed Jun. 24, 1999 now U.S. Pat. No. 6,379,909 which claims the priority benefits of Danish Patent Application Serial No. PA1998/00821 filed Jun. 24, 1998 and which also claims benefit of provisional application 60/090,895, filed Jun. 25, 1998. The present invention relates to a method of detecting a specific antibody in a liquid sample.

PRIOR ART

WO 94/11734 describes a two-site immunoassay for an antibody using a chemiluminescent label and a biotin bound ligand, said method comprising the steps of (a) mixing the liquid sample with a ligand antigen, antibody or hapten bound to biotin or a functional derivative thereof, an antibody directed against the antibody to be detected bound to paramagnetic particles and a chemiluminescent acridinium compound bound to avidin, streptavidin or a functional derivative thereof to form a solid phase complex, (b) magnetically separating the solid phase from the liquid phase, (c) initiating a chemiluminescent reaction, if any, in the separated solid phase and (d) analysing the separated solid phase for the presence of a chemiluminescent phase, which is indicative of the present of said antibody in the sample.

The prior art method is particularly suitable for measuring the concentration of specific immunoglobulins in body fluids, such as a specific immunoglobulin selected from the group of IgA, IgD, IgE, IgG, IgM and subclasses thereof.

The prior art method is also suitable for the detection and quantification of the total content of immunoglobulins in a class or subclass, such as IgA, IgD, IgE, IgG, IgM and subclasses thereof.

In a preferred embodiment of the prior art method the formation of the solid phase complex is effected in two steps, viz. a first step wherein the sample is mixed with the biotin bound ligand antigen, antibody or hapten and the antibody bound to paramagnetic particles so as to form a first solid phase complex, and a second step wherein the chemiluminescent acridinium compound is added to the first solid phase complex to form a second solid phase complex.

However, practical use of the prior art method has revealed the fact that in some applications of the method interference from other types of immunoglobulins and/or from other types of immunologically active serum components than the one to be measured occurs leading to errors in the results obtained.

The article "Capture assay for specific IgE", V. Olivieri et al, Journal of Immunological Methods, 157 (1993) 65–72 discloses an assay for the measurement of specific IgE in the serum of allergic patients using monoclonal anti-human IgE (coated to the wells of a microtiter plate) and biotinylated allergens in solution. In a single incubation IgE is bound to the solid phase through the Fc fragment and biotinylated allergens react with their specific IgE Fab regions. In a second step, streptavidin-horseradish peroxidase conjugate is added to reveal the amount of biotin fixed on the solid phase. The article studies the interference from high levels of non-specific IgE and from allergen-specific IgG. The assay is found to be unaffected by allergen-specific IgG.

WO 98/16829 discloses an assay, wherein an anti-immunoglobulin is coupled to a microtiter plate well, which is then washed. The test serum is then added to the well to capture all of total targeted immunoglobulin in the test sample. Then, the biological fluid sample is aspirated, and the microtiter plate is washed. The captured antibody on the microtiter plate is then exposed to biotinylated antigen, the plate is washed, and streptavidin/alkaline phosphatase conjugate is added, and the plate is washed again. The prior art assay may be used to monitor the effect of treatment on *H. pylori* infection with standard antibiotic therapy.

SUMMARY OF THE INVENTION

A first object of the invention is to provide a method of the type, wherein the targeted antibody is complexed to a Fc directed antibody coupled to a solid particle and to a Fab directed ligand, which does not suffer from the above explained drawback of interference from other components of the test sample.

This first object is achieved with the method of the invention, the essential new feature of the invention being that an additional sequence of separation and washing of the intermediate solid phase complex consisting of particle with reactant antibody and sample antibody is carried out prior to addition of ligand.

The method of the invention is based on the recognition that by introducing such an additional sequence of separation and washing, potentially interfering excess material from the liquid sample as well as potentially interfering excess component (ii) may be removed from the method thus eliminating the risk of interference of the said factors in subsequent steps. It has surprisingly been found that the additional sequence of separation and washing has reduced substantially and in some circumstances eliminated the technical problem of interference between different types of immunologically active serum components.

The reduction of the interference obtained involves a number of technical advantages. In particular, it allows a more precise measurement of problematic sera having a difficult and unpredictable ratio of mixture of antibodies. Furthermore, falsely positive identifications of an antibody may be avoided. Also, the reduction of interference allows precise measurements to be made in a wider antibody concentration range than with prior art methods.

A second object of the invention is to provide a method, which is capable of evaluating and/or predicting the effect of a Specific Allergy Vaccination (SAV).

This second object is obtained by the nature and the temporal development of the interference between different types of immunologically active serum components, e.g. antibodies, are used as parameters for evaluating/predicting the effect of a Specific Allergy Vaccination treatment. Thus, it has surprisingly been found that the said parameters hold valuable information about the immunological status of a person as well as the response of a person to a selected treatment scheme.

A third object of the invention is to provide a method of evaluating the immunological status of a subject.

The third object of the invention is obtained by the nature and the temporal development of the interference between different types of immunologically active serum components, e.g. antibodies, are used as a parameter for evaluating the immunological status of a subject, in particular evaluating/predicting the effect of allergy treatment, allergy vaccination treatment or Specific Allergy Vaccination treatment. Thus, it has surprisingly been found that the said parameter hold valuable information about the immunological status of a person as well as the response of a person to a selected treatment scheme.

A fourth object of the invention is to provide a method of evaluating the effect of allergy treatment of a subject.

The fourth object of the invention is obtained based on the recognition that the measurement obtained with the subassays 1, A and C, i.e. a measurement, which is carried out in the presence of interfering factors in the sample, is particular useful for evaluating the effect of allergy treatment, allergy vaccination treatment and Specific Allergy Treatment (SAV). Thus, the measurement obtained with this method is obtained under conditions, which correspond to in vivo conditions, and hence is a more physiological and clinical relevant measurement for evaluating treatment effects.

FIRST ASPECT OF THE INVENTION

A preferred embodiment of the first aspect of the invention is characterized in that component (iii) of step (r'), (r) or (r") and component (iv) of step (s'), (s) or (s"), respectively, are added in one operation.

A first alternative embodiment of the first aspect of the invention is characterized in that the three-component solid phase complex formed in step (r'), (r) or (r") prior to subjecting it to step (s'), (s) or (s"), respectively, is washed to remove non-complex bound compounds.

SECOND ASPECT OF THE INVENTION

Specific allergy Vaccination (SAV), formerly known as Specific Immunotheraphy or Hyposensitization, has been used for the treatment of Type 1 IgE mediated allergic disease since the beginning of this century.

The general benefits obtained through SAV are: a) reduction of allergic symptoms and medicine consumption, b) improved tolerance towards the allergens in the eyes, nose and lungs and c) reduced skin reactivity (early and late phase reactions).

The basic mechanism behind the improvement obtained by SAV is unknown, but a number of common features can be extracted from the numerous SAV studies performed in the last decades: 1) the amount of total IgE is unchanged during the treatment period, 2) the amount of allergen specific IgE increases transiently during updosing, then it falls back to the initial (pretreatment) level, 3) the epitope specificity and affinity of IgE remains unchanged, 4) allergen specific IgG, in particularly IgG4, raises sharply during SAV, 5) a new Th0/1 response is apparently initiated and 6) the Th2 response seem unchanged. There is no correlation between the effect induced by SAV and the onset of specific IgG.

SAV induces a new immune response which matures during the treatment period (Th0/1 T-cells are recruited, an allergen specific IgX (X may be A1, A2, G1, G2, G3, G4, M or D) is initiated). As the affinity (or amount/affinity) of the new antibody response, IgX, has matured, IgX may compete efficiently with IgE for the allergen(s), inhibiting the "normal" Th2 based allergic response characterised by the cross-linking of receptor bound IgE on the surface of mast-cells and basophils. Hence, clinical symptoms will gradually be reduced.

The present invention is based on the hypothesis that is one measures the amount of specific IgE in the presence and absence of competing compounds (IgX and/or any other interfering substance), a measure for the competitive capability of immune responses in the individual patient may be calculated and this measure would correlate with an appropriate effect parameter.

Most prior art "quantitative" IgE assays measure IgE in the absence of competing substances. The present invention describes the measurement of IgE in the presence and absence of any (serum originating) competing substance. Thus, the methods referred to in FIGS. 2a–c measure IgE in the absence of competing agents, whereas the method defined in step (i'), (i), (i"), (y'), (y) and (y"), respectively, measure IgE in the presence of competing agents.

It is believed that the mode of action of the method of the invention may be explained as follows: If SAV induces a response which competes with IgE for the binding of the allergen it should be possible to measure the effect of the treatment by comparing IgE determined by the above stated two methods. If the two methods produce the same result no interfering substance has been induced and there is no effect. Furthermore, if the measurement of the latter method (in the presence of competing substances) is lower than the measurement of the former method (in the absence of competing substances) a competing response has been mounted and there is an effect of the treatment.

In the second aspect of the invention, two subassays are used in the method, viz. subassays, wherein the reaction between sample antibody and allergen is effected in the absence (subassay (h'), (h), (h"), (x'), (x) and (x")) and presence (subassay (i'), (i), (i"), (y'), (y) and (y")) of the other sample constituents, respectively.

In subassays (h) and (h"), the chemiluminescent label may be an acridinium compound.

A preferred embodiment of the subassays (h'), (h) and (h") is characterized in that in step (a'), (a) or (a") components (i), (ii) and (iii) are mixed in one operation (FIG. 3b).

A first alternative embodiment of the subassays (h'), (h) and (h") is characterized in that in step (a'), (a) or (a") components (i) and (ii) are mixed in a first operation and that component (iii) is added in a second operation (FIG. 3c).

A second alternative subassays (h'), (h) and (h") is characterized in that in step (a'), (a) or (a") components (i) and (iii) are mixed in a first operation and that component (ii) is added in a second operation (FIG. 3a).

A preferred embodiment of the second aspect of the invention is characterized in that step (ia'), (ia), (ia"), (ya'), (ya) or (ya") is carried out by mixing components (i) and (ii), then adding component (iii), and finally adding component (iv), if added.

Another preferred embodiment of the second aspect of the invention is characterized in that step (ia'), (ia), (ia"), (ya'), (ya) or (ya") is carried out by mixing components (i), (ii) and (iii), and then adding component (iv), if added.

A further preferred embodiment is characterized in that the comparison of step (j'), (j), (j"), (z') or (z") is carried out by calculating the ratio of the measurements of the said two steps. Alternatively, the comparison is carried out by calculating the difference between the two measurements.

Still a further embodiment of the invention is characterized in that the comparison of step (j'), (j), (j"), (z'), (z) or (z") is carried out at a number of points in time at the start of and during the treatment period, and that any temporal change, which may be observed, is used as a basis for evaluating and/or predicting the effect of the treatment.

THIRD ASPECT OF THE INVENTION

The third aspect of the invention is based on the same recognitions and hypothesis as the second aspect, the difference being that the third aspect is not limited to any specific immunoassay procedure. Also, according to the third aspect the assay may be used to predict the effect of all types of allergy treatment.

The interrelating of the two measurements obtained may be carried out by calculating the ratio of or the difference between the measurements.

The term "allergy treatment" means any treatment of allergy. The term "allergy vaccination treatment" means any vaccination treatment of allergy. The term "Specific Vaccination Treatment (SAV)" is described above.

Definitions

In the present invention the expressions "the antibody of the sample" and "sample antibody" may mean a specific immunoglobulin, preferably a specific immunoglobulin from the classes IgA, IgD, IgE, IgG, IgM and subclasses thereof. In general, the said antibody may be any blood serum or plasma component, which is capable of interfering specifically with the interaction between immunoglobulines and a ligand in the form of an antigen, an antibody or hapten, e.g. enzyme inhibitors and receptors.

The term "liquid sample" means any liquid or liquefied sample, including solutions, emulsions, dispersions and suspensions. The sample may be a biological fluid, such as blood, plasma, serum, urine, saliva and any other fluid, which is excreted, secreted or transported within a biological organism.

The expression "ligand in the form of an antigen, an antibody or a hapten" may be any immunologically active substance. "Antigen" may be an allergen, e.g. pollen from trees, grass, weeds etc., mould allergens, allergens from acarids (mites) and animals, such as cat, dog, horse, cattle and bird, allergens of stinging insects and inhaled allergens originating from insects, and food allergens; "antibody" may be a monoclonal or polyclonal antibody, including recombinant and fragmented antibodies; and "hapten" may be carbohydrate moieties or fragments thereof, enzyme inhibitors or drugs, e.g. penicillin or a derivative thereof.

The expression "labelled ligand" means any ligand comprising a labelled atom or part, e.g. a radioactive atom label.

The expressions "label compound" means any suitable label system conventionally used in immunoassays comprising luminescent labels, chemiluminescent labels, enzyme labels, radioactivity labels, fluorescent labels, and absorbance labels.

The term "carrier" means any solid support, which may be used in an immunoassay, e.g. a microtiter plate, a particle, a tube, a sponge of a polymer material (matrix), etc.

The term "solid particle" means any particulate matter, which can be suspended in a liquid, e.g. glass beads, metal, e.g. iron particles, particles of polymer material, etc.

The separation of the solid phase complex from the liquid phase may, depending on the type of solid particle used, be carried out by i.a. magnetic separation, filtration, sedimentation, centrifugation, chromatography, column chromatography.

The term "solid paramagnetic particle" means any paramagnetic particle, which may be dispersed or suspended in a liquid medium, e.g. "Biomag" particles (iron oxide particles coated with amine terminated groups) sold by Advanced Magnetics Inc., U.S.A., and "Dynabeads" (iron oxide covered with a polymer) sold by Dynal A. S., Norway.

The term "reactant antibody" means any antibody or other biospecific reagent capable of reacting with the sample antibody comprising monoclonal and polyclonal antibodies, including recombinant and fragmented antibodies, e.g. a monoclonal antibody, "MAb A 5697-1A3 (920325) supplied by BioInVent International AB, Sweden, "Protein A" or "Protein G" supplied by Sigma Chemical Company, Saint Louis, USA.

The chemiluminescent compound is preferably an acridinium compound, such as N-hydroxy-succinimide dimethylacridiniumestar (NHS-DMAE). Avidin/streptavidin and DMAE may be coupled according to the methods of weeks et al., Clinical Chem., 29, 1474–1479 (1983). Other examples of chemiluminescent compounds suitable for use in the present invention are luminol, lucingenin and lophine.

In the following, the invention will be described in further detail with respect to the figures, wherein FIG. 1a-b are diagrammatic representations of two embodiments (Prior Art Method A and B) of the prior art assay disclosed in WO 94/11734.

FIG. 2a-c are diagrammatic representations of three preferred assays of the present invention.

FIG. 3a-c are diagrammatic representations of three preferred assays according to the first aspect of the invention.

Figure 1A:
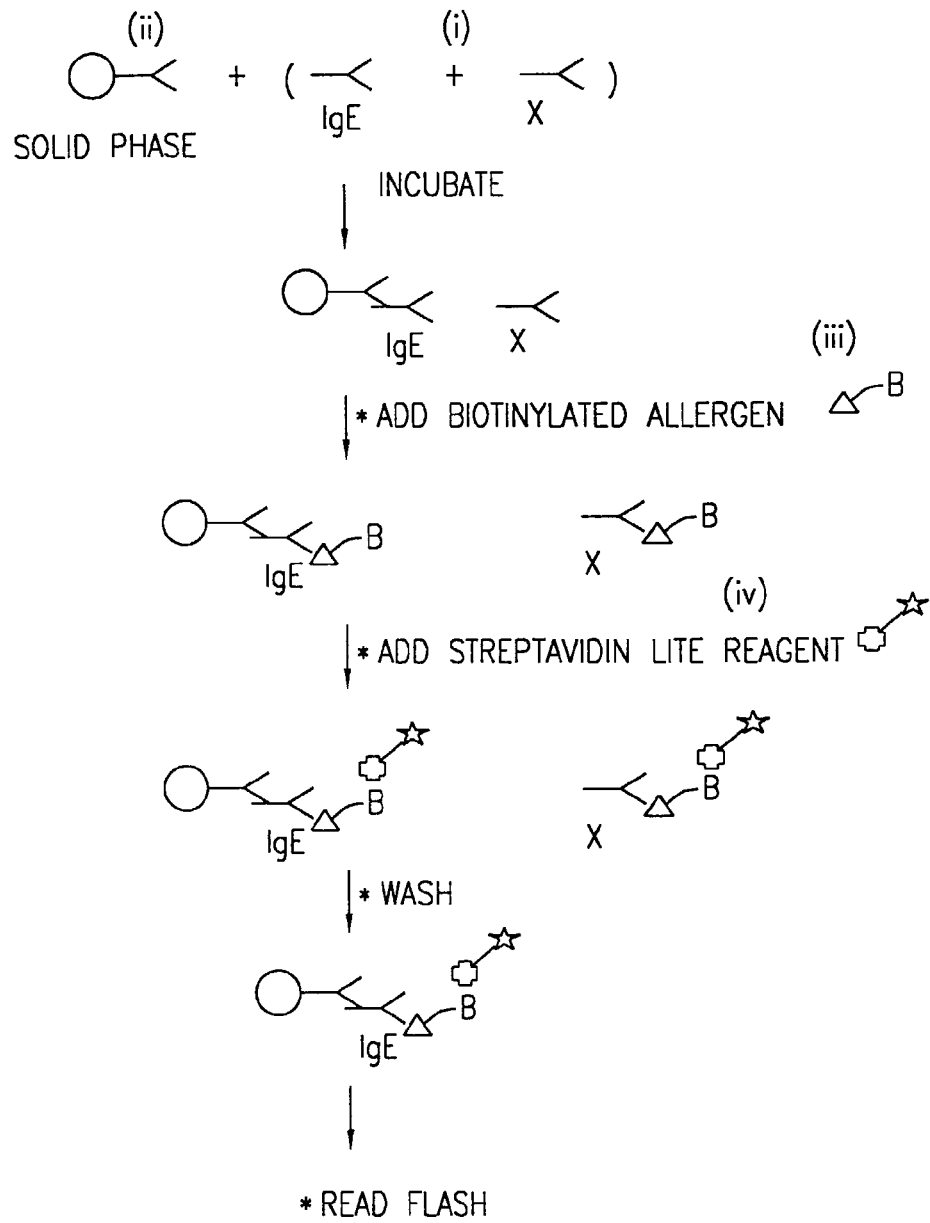

FIG. 1a shows the principle of one embodiment of the assay disclosed in WO 94/11734. In the assay the antibody to be detected (specific IgE) in the sample (i) is mixed with a reactant antibody bound to a paramagnetic particle (ii) to form a two-component complex, which is incubated, and then a biotinylated allergen (iii) is added to form a three-component complex, which is incubated, and then a chemiluminescent acridinium compound bound to avidin/streptavidin (iv) is added to form a four-component complex, which is washed, and the chemiluminescence of the washed complex is then measured.

Figure 1B:
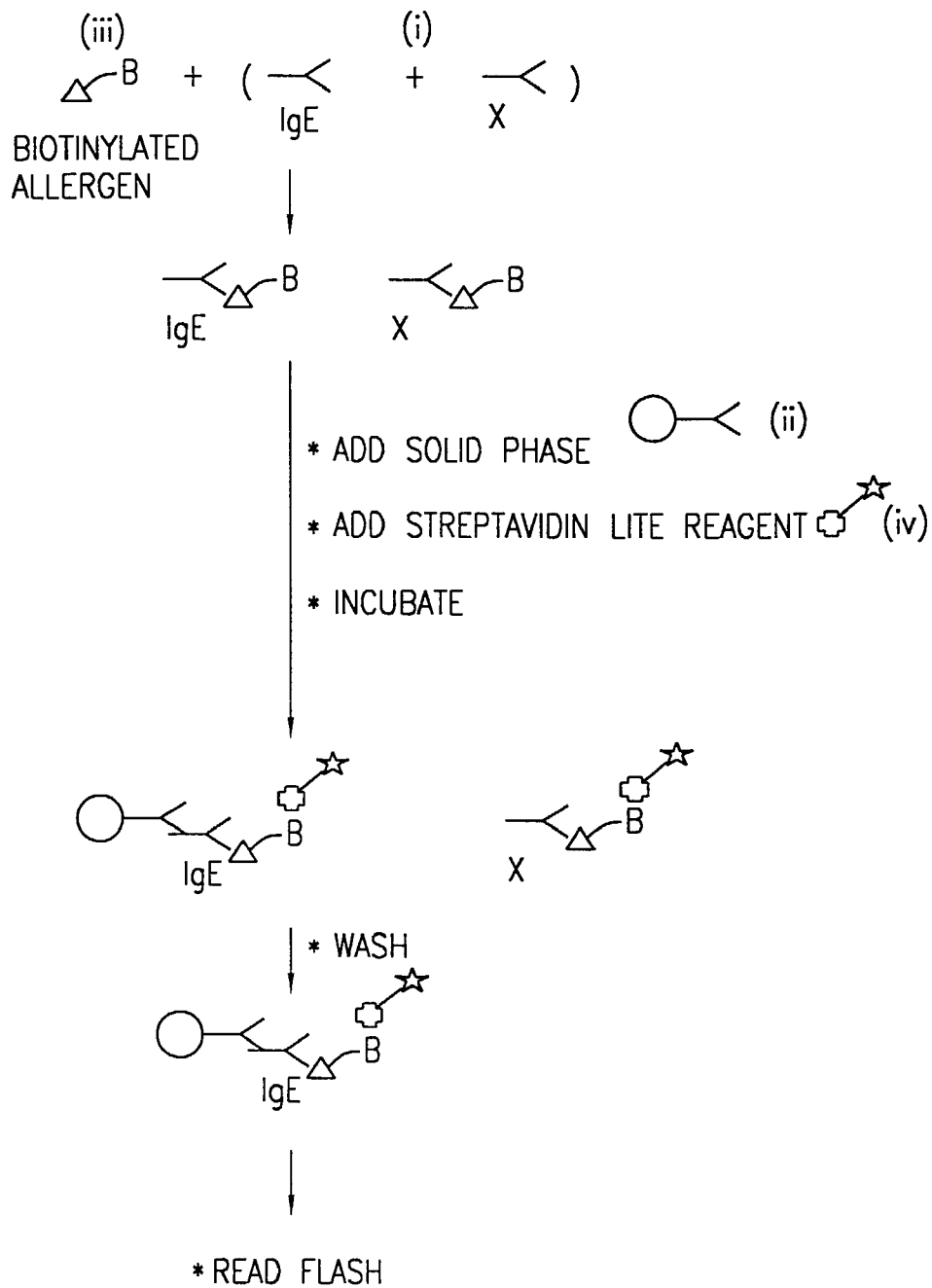

FIG. 1b show another embodiment of the prior art assay, wherein components (i) and (iii) are mixed to form a two-component complex, and wherein components (ii) and (iv) are then added, and the resulting mixture is incubated to form a four-component complex, which is washed and subjected to chemiluminescence measurement.

In the assays of FIGS. 1a and 1b all constituents of the sample, including any cross-reacting IgE antibodies and non-IgE antibodies specific to the allergen, are present in the subsequent reactions leading to the formation of the four-component complex.

Figure 2A:
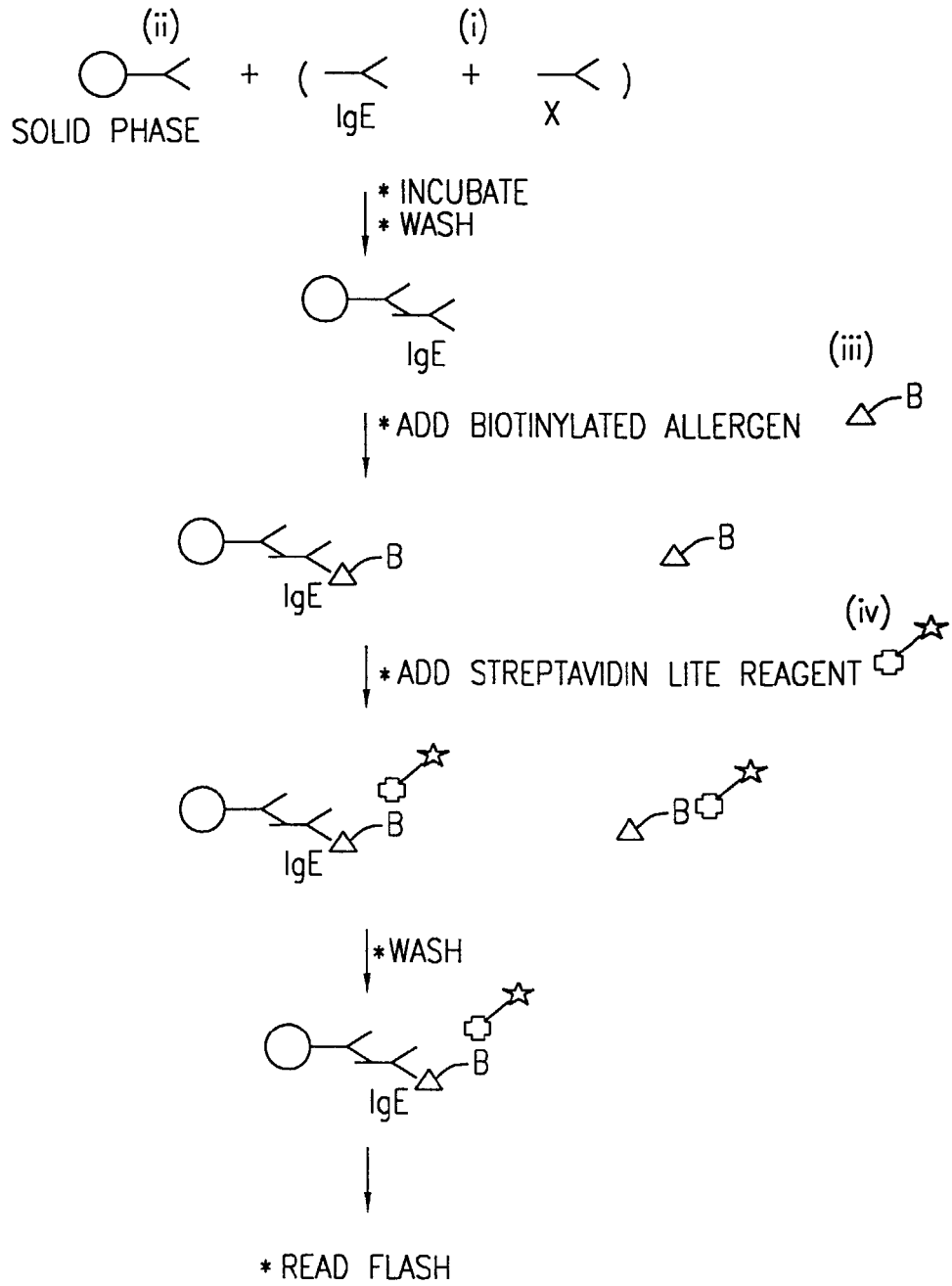

FIG. 2a shows a preferred embodiment of the second aspect of the invention, wherein components (i) and (ii) are mixed and incubated to form a two-component complex, which is washed. The component (iii) is added to form a three-component complex, after which component (iv) is added to form a four-component complex, which is washed and subjected to chemiluminescence measurement.

Figure 2B:
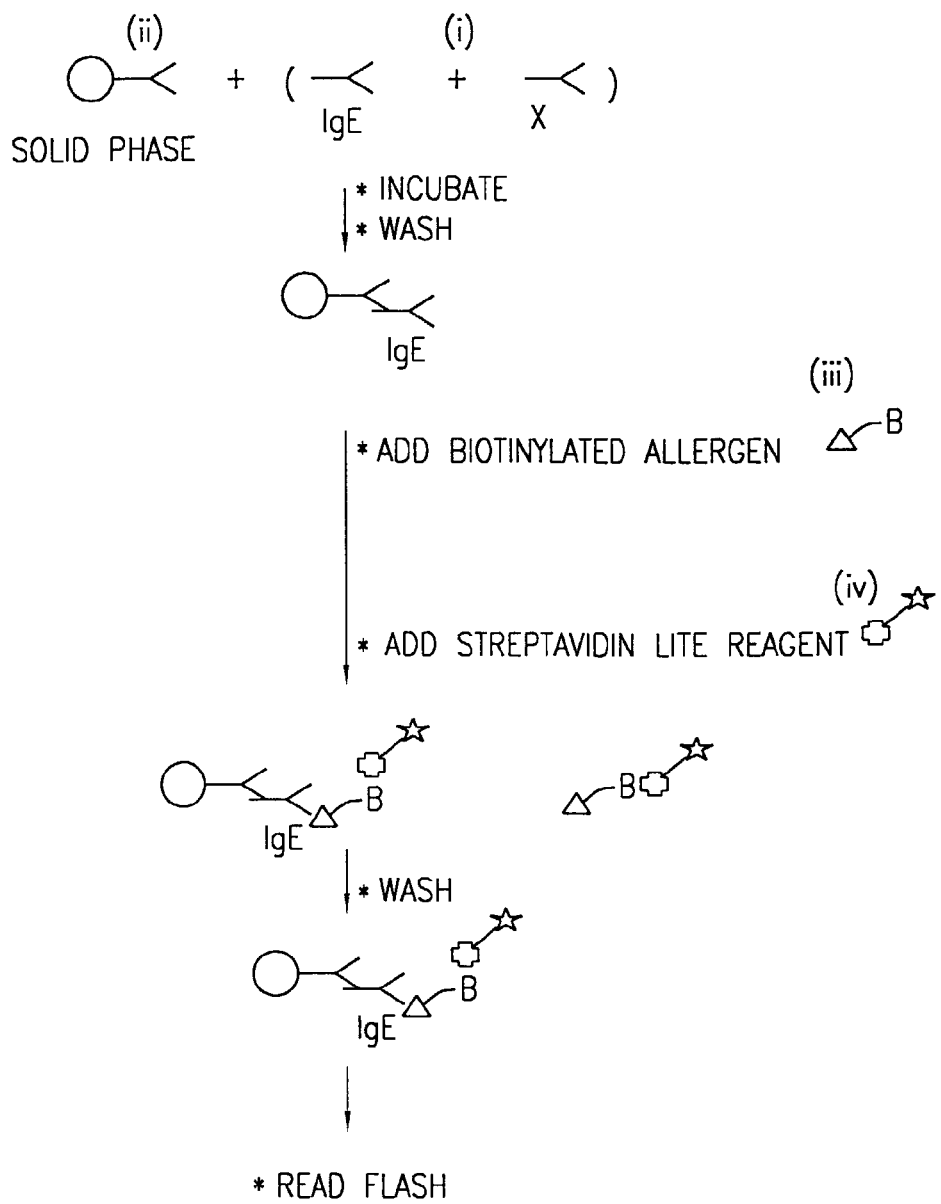

FIG. 2b shows another preferred embodiment of the second aspect of the invention, which corresponds to that shown in FIG. 2a except that components (iii) and (iv) are added in one operation.

Figure 2C:
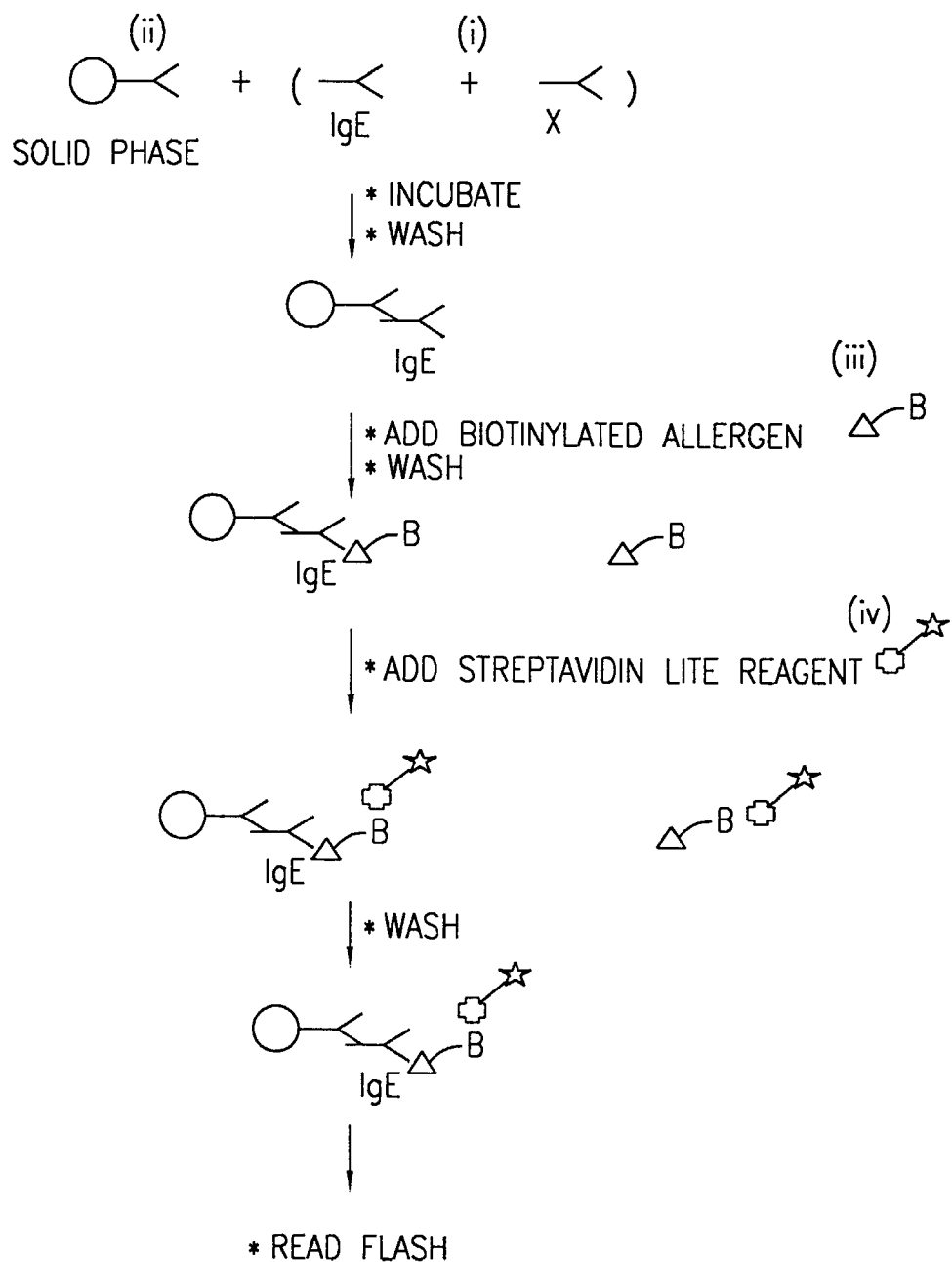

FIG. 2c shows a further preferred embodiment of the second aspect of the invention, which corresponds to that shown in FIG. 2a except that the three-component complex formed is subjected to a washing step before the addition of component (iv).

In the assays of FIGS. 2a, 2b and 2c the constituents of the sample, including any cross-reacting IgE antibodies and non-IgE antibodies specific to the allergen, are removed after reaction with component (ii) and are hence absent in the subsequent reaction steps leading to the formation of the four-component complex.

Figure 3A:
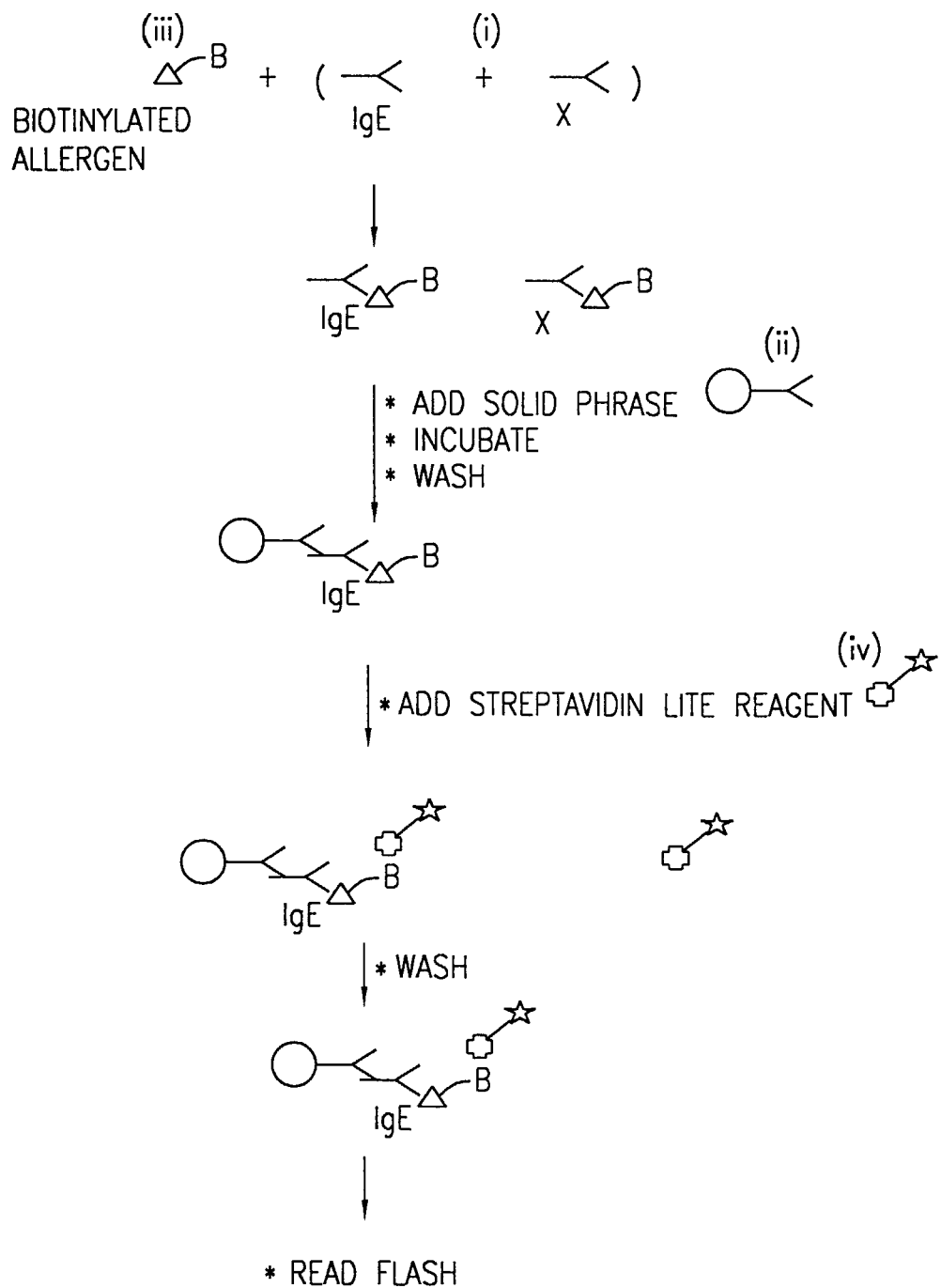

FIG. 3a shows a preferred embodiment of the subassays (h'), (h) and (h"), wherein components (i) and (iii) are mixed in a first operation to form a two-component complex, to which component (ii) is then added in a second operation, and the resulting mixture is incubated to form a three-component complex, which is washed before adding component (iv) to form a four-component complex, which is then washed before subjecting it to chemiluminescence measurement.

Figure 3B:
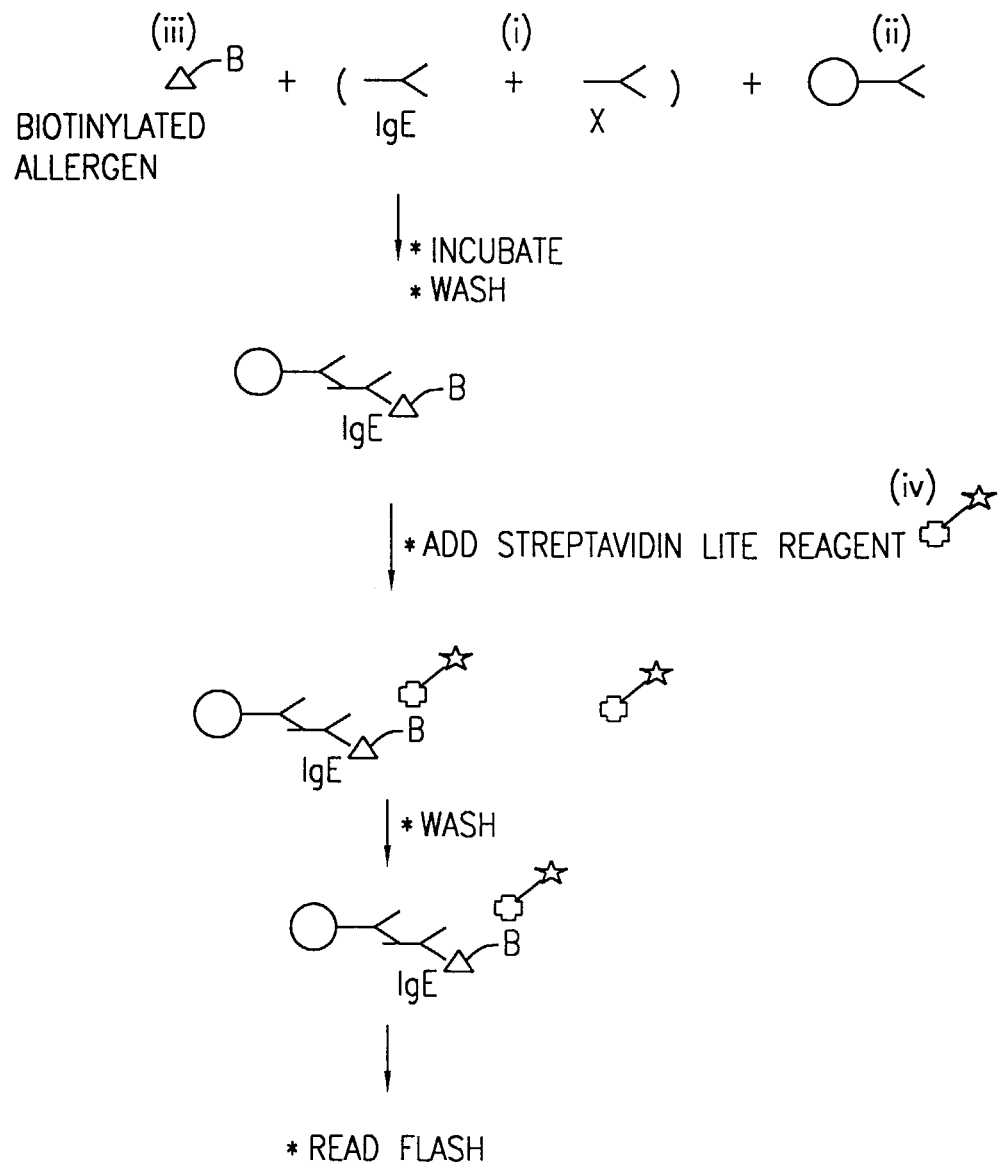

FIG. 3b shows another preferred embodiment of subassays (h'), (h) and (h"), wherein the components (i), (ii) and (iii) are added in one operation to form a three-component complex, which is then washed before adding component (iv) to form a four-component complex, which is then washed before subjecting it to chemiluminescence measurement.

Figure 3C:
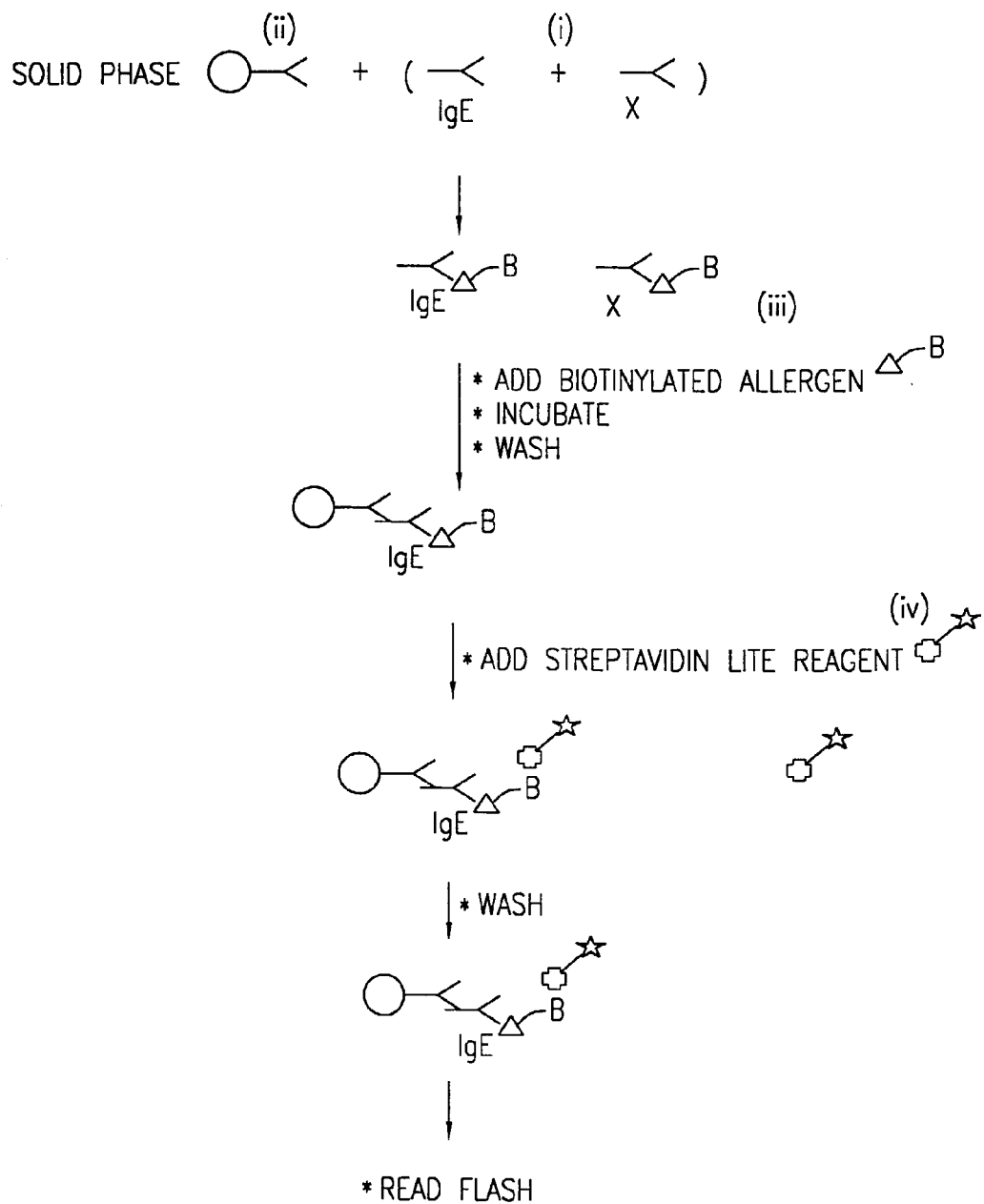

FIG. 3c shows a further preferred embodiment of subassays (h'), (h) and (h"), wherein components (i) and (ii) are mixed to form a two-component complex, to which component (iii) is then added to form a three-component complex, which is washed before adding component (iv) to form a four-component complex, which is also washed before subjecting it to chemiluminescence measurement.

In the assays of FIGS. 3a, 3b and 3c the constituents of the sample, including any cross-reacting IgE antibodies and non-IgE antibodies specific to the allergen, are removed after reaction with components (ii) and (iii) and are hence absent in the subsequent reaction step leading to the formation of the four-component complex.

In the following the invention will be described in further detail with reference to the examples.

PREPARATION OF REAGENTS

Biotinylated *Dermatophagoides pteronyssinus*

*Dermatophagoides pteronyssinus* extract, (ALK-ABELLÓ A/S, Hrsholm, Denmark) is biotinylated in the molar ratio of 30:1. Biotin amidocaproate N-hydroxysuccinimide ester (Biotin-XX-NHS, Clontech, USA) is dissolved in Dimethylformamide (Merk) to a final concentration of 25 mg/ml. 55.4 µl of this solution of Biotin-XX-NHS is added to 1 ml of 2.44 mg/ml *Dermatophagoides pteronyssinus* in 0.1 M $NaHCO_3$, pH 8.5. The reagents are incubated for 15 minutes at 25° C. in an "end over end" mixer. The biotinylated extract is purified from unbound biotin by size exclusion chromatography on a PD10-column (Pharmacia). The fraction containing the allergens is collected. The biotinylated *Dermatophagoides pteronyssinus* is diluted with Phosphate buffered saline, pH 7.2 (PBS), containing 0.1% human serum albumin (Sigma) and 0.09% $NaN_3$ (Merck).

Biotinylated *Alternaria alternata*

*Alternaria alternata* extract, (ALK-ABELLÓ A/S, Hrsholm, Denmark) is biotinylated in the molar ratio of 30:1. Biotin amidocaproate N-hydroxysuccinimide ester (Biotin-XX-NHS, Clontech, USA) is dissolved in Dimethylformamide (Merck) to a final concentration of 25 mg/ml. 38.6 µl of this solution of Biotin-XX-NHS is added to 1 ml of 1.7 mg/ml *Alternaria alternata* in 0.1 M $NaHCO_3$, pH 8.5. The reagents are incubated for 15 minutes at 25° C. in an "end over end" mixer. The biotinylated extract is purified from unbound biotin by size exclusion chromatography on a PD10-column (Pharmacia). The fraction containing the allergens is collected. The biotinylated *Alternaria alternata* is diluted with Phosphate buffered saline, pH 7.2 (PBS), containing 0.1% human serum albumin (Sigma) and 0.09% $NaN_3$ (Merck).

Biotinylated *Betula verrucosa* (Silver birch)

*Betula verrucosa* pollen extract, (ALK-ABELLÓ A/S, Hrsholm, Denmark) is biotinylated in the molar ratio of 10:1. Biotin amidocaproate N-hydroxysuccinimide ester (Biotin-XX-NHS, Clontech, USA) is dissolved in Dimethylformamide (Merck) to a final concentration of 25 mg/ml. 33.5 µl of this solution of biotin-XX-NHS is added to 1 ml of 4.4 mg/ml *Betula verrucosa* in 0.1 M $NaHCO_3$, pH 8.5. The reagents are incubated for 15 minutes at 25° C. in an "end over end" mixer. The biotinylated extract is purified from unbound biotin by size exclusion chromatography on a PD10-column (Pharmacia). The fraction containing the allergens is collected. The biotinylated *Betula verrucosa* is diluted with Phosphate buffered saline, pH 7.2 (PBS), containing 0.1% human serum albumin (Sigma) and 0.09% $NaN_3$ (Merck).

Preparation of Streptavidin Acridinium Ester Label

Streptavidin (Boehringer Mannheim) was conjugated with NSP-DMAE-NHS (2',6'-dimethyl-4'-(N-succinimidyloxy-carbonyl)phenyl-10-(3-sulfopropyl)-acridinium-9-carboxylate) using a modified method of Weeks et al. (ref. 1).

Preparation of Streptavidin-acridinium Ester Label (lite reagent):

NSP-DMAE-NHS (Chiron Diagnostics, MA, USA) is dissolved in Dimethylformamide (Merck) to a final concentration of 1 mg/ml. 0.5 ml of this solution is added to 1.7 ml 5.88 mg/ml streptavidin in 0.1 M Sodium Phosphate buffer, 0.15 M NaCl, pH 8.5. The reagents are incubated for 30 minutes at 25° C. with stirring. After incubation 0.4 ml 20 mg/ml 6-Amino-n-hexanoic acid (Sigma) is added. To remove unbound DMAE the solution is loaded onto a PD-10 column (Pharmacia, Uppsala, Sweden). The conjugated streptavidin is eluted with Phosphate buffered saline, pH 7.2 (PBS) and the fraction containing the conjugated streptavidin is collected. The conjugated streptavidin is diluted to a final concentration with Phosphate buffered saline, pH 7.2 (PBS) containing 0.1% HSA (Sigma), 1% Tween 20 (Merck) and 0.09% $NaN_3$.

Immobilization of Antibody to Paramagnetic Particles:

6.5 g paramagnetic particles (Chiron Diagnostics, MA, USA) are washed 3 times in 650 ml 0.01 M acetate buffer pH 5.5 using magnetic separation. The particles are activated in 6.25% glutaraldehyde (Merck), 0.01 M acetate buffer pH 5.5 for 3 hours at 25° C. The particles are washed 6 times in 650 ml acetate buffer pH 5.5. The particles are coupled with 1625 mg monoclonal anti-IgE antibody (Bio-Invent International AB, Sweden) specific against the IgE Fc domain, for 16 hours at 25° C. The particles are washed twice in 650 ml 0.01 M phosphate buffer pH 7.4. Blocking of excess of active groups is performed with 1083 mg HSA (Sigma) dissolved in 0.01 M phosphate buffer pH 7.4 for 20 hours at 25° C. The particles are washed in 650 ml 0.01 M phosphate buffer pH 7.4 followed by 3 washes in 650 ml 1 M NaCl (Merck). The particles are washed 3 times in 0.01 M phosphate buffer pH 7.4 followed by a wash with 650 ml PBS pH 7.4, 0.1% HSA (Sigma). The particles are resuspended in 325 ml and heat treated for 16 hours at 50° C. The particles are washed 4 times in 650 ml 0.01 M phosphate pH 7.4, 0.1% HSA. The particles are heat treated at 37° C. for 7 days in 650 ml 0.01 M phosphate pH 7.4, 0.1% HSA with a buffer exchange on day 3 and day 5. The particles are diluted to a final concentration with Phosphate buffered saline, pH 7.2 (PBS) containing 0.1% HSA (Sigma) and 0.09% $NaN_3$.

Washing Buffer for Assays:

The washing buffer for assays is composed of 200 mM Potassium phosphate buffer, pH 7.4, 100 mM Potassium chloride, 0.1% Tween 20 and 0.09% $NaN_3$. All reagents are from Merck.

Example 1

Determination of Specific Antibody (Specific IgE)

Determination of specific IgE antibodies against *Betula verrucosa* (Silver birch) allergen was performed by three different methods using the reagents described above in the working dilutions defined in each method. The three methods used were Prior Art Method B (FIG. 1*b*), Method 1 according to the invention (FIG. 2*a*) and Submethod 1 according to the invention (FIG. 3*a*).

Prior Art Method B

This method is performed on Ciba Corning ACS:180 Benchtop Immunoassay Analyzer described in ref. 2. The analyzer is custom equipped with a 40 second time cycle software to give incubation times of two times the normal. 50 µl of sample and 50 µl of biotinylated *Betula verrucosa* allergen diluted 1:1500 are dispensed by the sample probe into the cuvette. When the cuvette after 12 minutes of incubation reaches reagent probe R2, 100 µl of paramagnetic particles diluted 1:20 and 200 µl of lite reagent diluted 1:10000 are dispensed simultaneously and the cuvette moves down the track. The magnets and the wash station are reached after additional 12 minutes and 40 seconds incubation. Wash with 750 µl deionized water is performed twice. After completion of the wash cycle the paramagnetic particles are resuspended in 300 µl 0.5 g/l $H_2O_2$ in 0.1 M $HNO_3$. The cuvette enters the luminometer chamber and in front of the photomultiplier 300 µl 25 mM NaOH solution is added and the photons of light emitted are measured and quantitated and expressed as relative light units (RLU). The amount of RLU is proportional to the amount of IgE in the sample. The time from sample dispension to first result is 30 minutes and a new result follows every 40 second. Results were expressed as RLU experiment/RLU background, where RLU background was the chemiluminescent reaction in the absence of IgE.

Method 1

This method is performed on a modified version of Ciba Corning ACS:180 Benchtop Immunoassay Analyzer described in ref. 2. 25 µl of sample is dispensed by the sample probe into the cuvette and immediately after this 100 µl of paramagnetic particles diluted 1:20 is dispensed by a fixed probe. After 8 minutes of incubation paramagnetic particles are magnetically separated and washed once with 1 ml of washing buffer. The paramagnetic particles are resuspended in 100 µl of washing buffer and 50 µl of biotinylated *Betula verrucosa* allergen diluted 1:1500 is added to the cuvette. After 10 minutes of incubation, 100 µl of lite reagent diluted 1:5000 is dispensed with a fixed probe and after additional 8 minutes of incubation the paramagnetic particles are magnetically separated and washed 3 times with 1 ml of washing buffer. After completion of the wash cycle the paramagnetic particles are resuspended in 300 µl 0.5 g/l $H_2O_2$ in 0.1 M $HNO_3$. The cuvette enters the luminometer chamber and in front of the photomultiplier 300 µl 25 mM NaOH solution is added and the photons of light emitted are measured and quantitated and expressed as relative light units (RLU). The amount of RLU is proportional to the amount of IgE in the sample. Results were expressed as RLU experiment/RLU background, where RLU background was the chemiluminescent reaction in the absence of IgE.

Submethod 1

This method is performed manually in 5 ml polystyrene test tubes (Sarstedt). 25 µl of sample is mixed with 50 µl of biotinylated *Betula verrucosa* allergen diluted 1:50. After 12 minutes of incubation at 37° C., 100 µl of paramagnetic particles diluted 1:20 are added and the mixture is incubated for 5 minutes and 30 seconds at 37° C. before the paramagnetic particles are magnetically separated and washed once with 3 ml of washing buffer using a Magic Lite Multitube Washer (ALK-ABELLÓ A/S, Hrsholm, Denmark). The paramagnetic particles are resuspended in 200 µl of lite reagent diluted 1:10000 and incubated for 7 minutes and 30 seconds at 37° C. before the paramagnetic particles are magnetically separated and washed 2 times with 3 ml of washing buffer using a Magic Lite Multitube Washer (ALK-ABELLÓ A/S, Hrsholm, Denmark). The paramagnetic particles are resuspended in 100 µl of deionized water and the chemiluminescent reaction is measured in a Magic Lite Analyzer IT (ALK-ABELLÓ A/S, Hrsholm, Denmark) by adding first 300 µl 0.5 g/l $H_2O_2$ in 0.1 M $HNO_3$ and then 300 µl 25 mM NaOH solution. The photons of light emitted are measured and quantitated and expressed as relative light units (RLU). The amount of RLU is proportional to the amount of IgE in the sample. Results were expressed as RLU experiment/RLU background, where RLU background was the chemiluminescent reaction in the absence of IgE.

Figure 4:
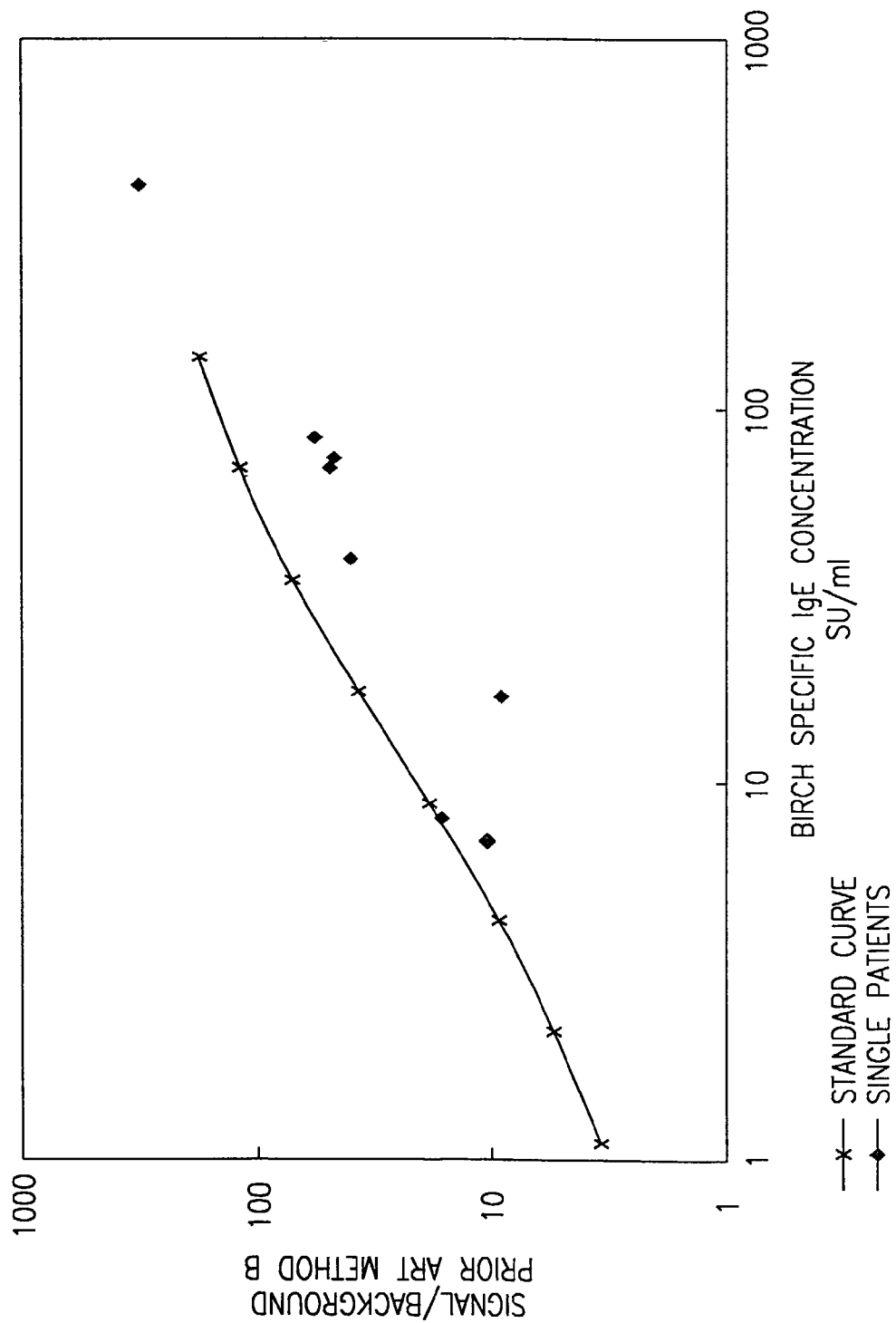
FIG. 4-6 show the chemiluminescence level as a function of the concentration of specific IgE for Prior Art Method B, Method 1 of the invention and Submethod 1 of the invention, respectively.
Figure 5:
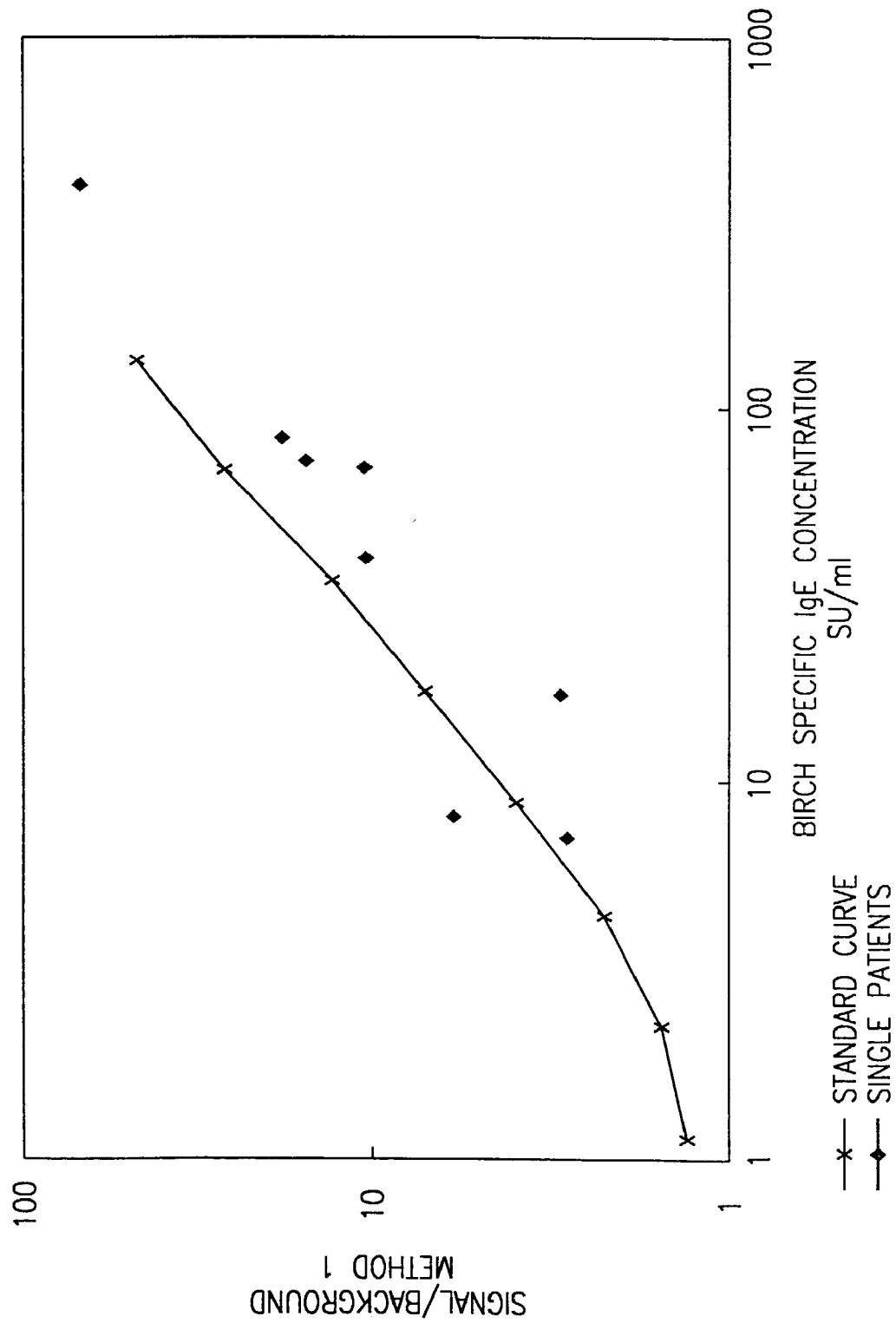
Figure 6:
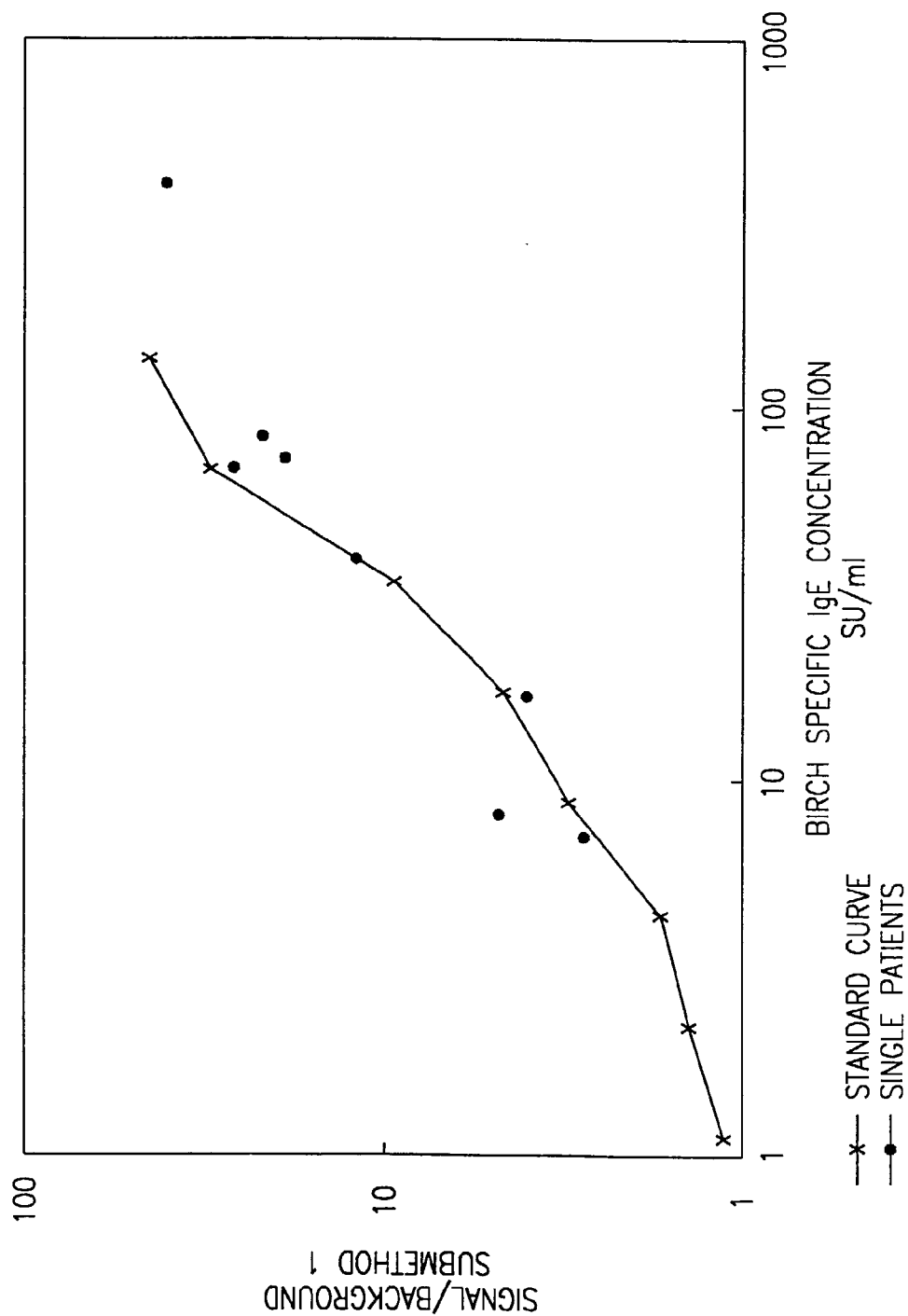

A serum pool of 5 birch pollen sensitive patients was serially diluted by a factor two from 140 SU/ml to 1.1 SU/ml to give 8 samples. These 8 samples were assayed together with a negative sample (background) and 8 samples from birch pollen sensitive individuals in each of the 3 above described methods, see FIGS. 4, 5 and 6, respectively. It can be concluded that all assayed samples can be detected as positive using all three methods.

Example 2

Interference with Specific Antibodies from Other Classes (IgG)

Determination of specific IgE against *Betula verrucosa* (Silver birch) allergen was performed by the three different methods as described in Example 1 in the presence of varying amounts of competing specific antibodies. More specifically, a serum pool of 5 birch pollen sensitive patients was mixed in a 1:5 ratio with IgE negative serum containing different titers of rabbit polyclonal anti-*Betula verrucosa* antibody (ALK-ABELLÓ A/S, Hrsholm, Denmark). The control contained no rabbit antibody.

Figure 7:
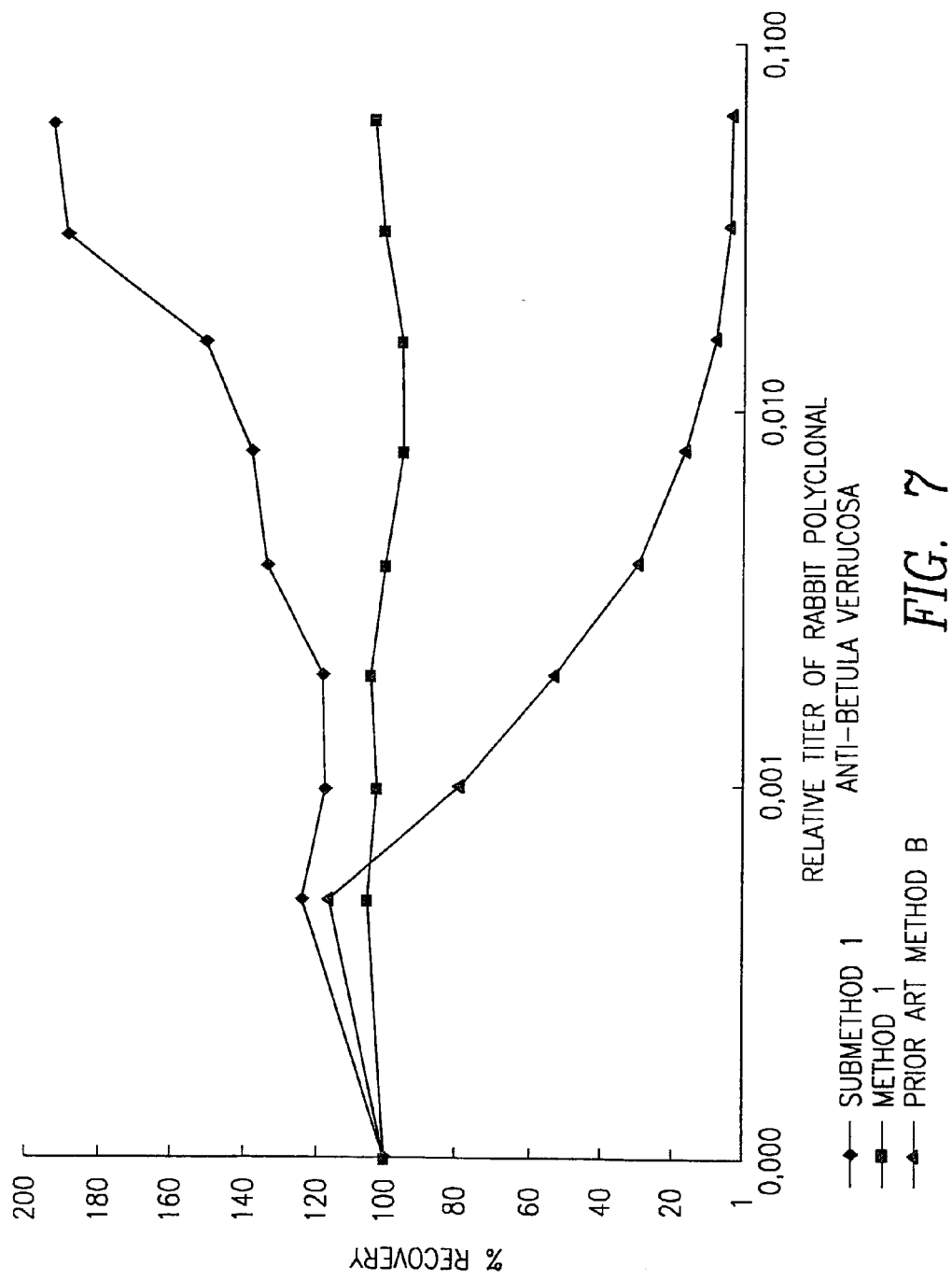
FIG. 7 shows the relative chemiluminescence level as a function of the content of interfering antibodies for Prior Art Method B, Method 1 of the invention and Submethod 1 of the invention.
Figure 8:
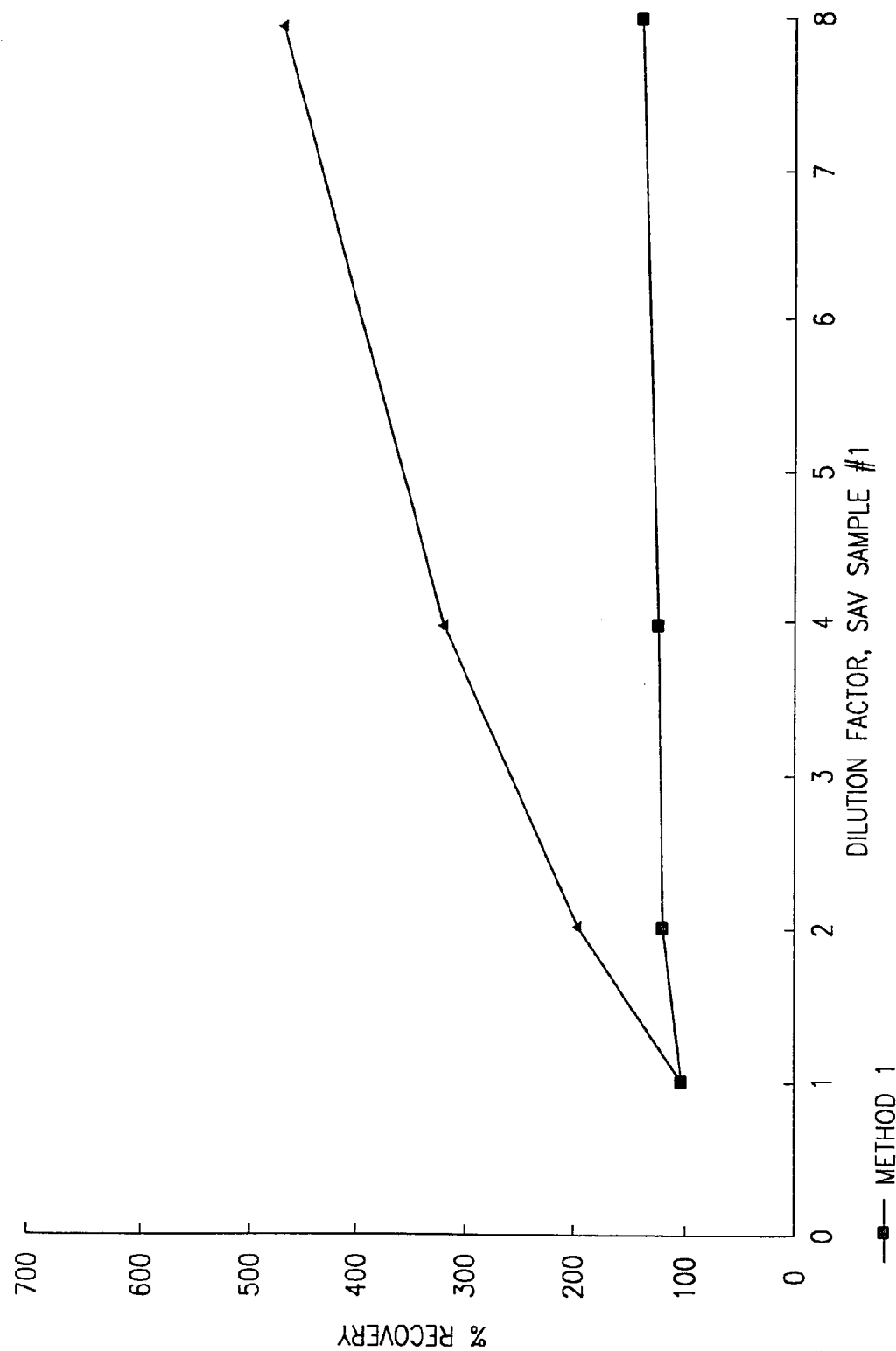
FIG. 8-12 show the calculated chemiluminiescnce level relative to the expected level as a function of dilution factor for Prior Art Method B and Method 1 of the invention for four samples from patients subjected to Specific Allergy Vaccination and one reference sample (FIG. 12).
Figure 9:
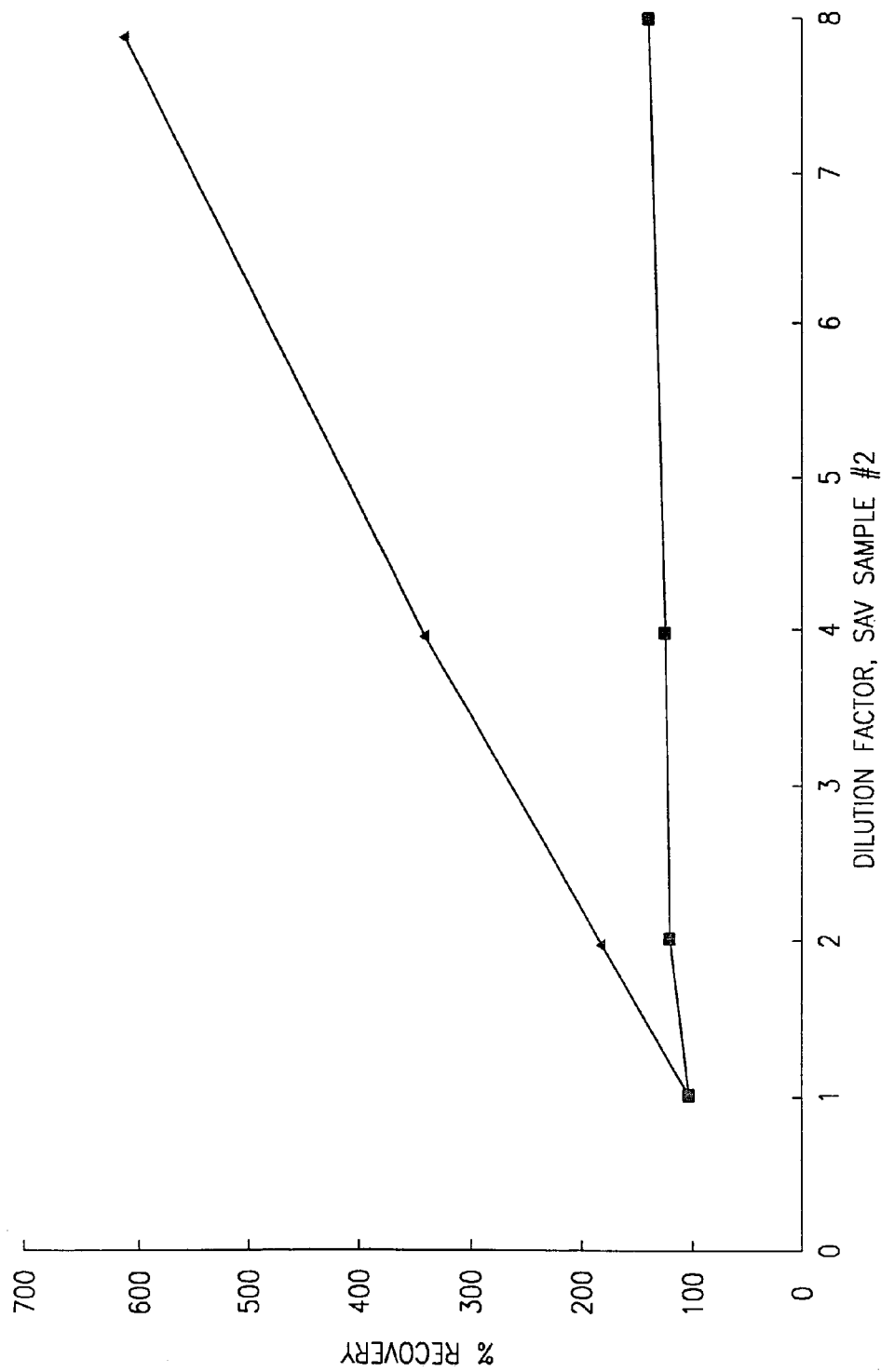
Figure 10:
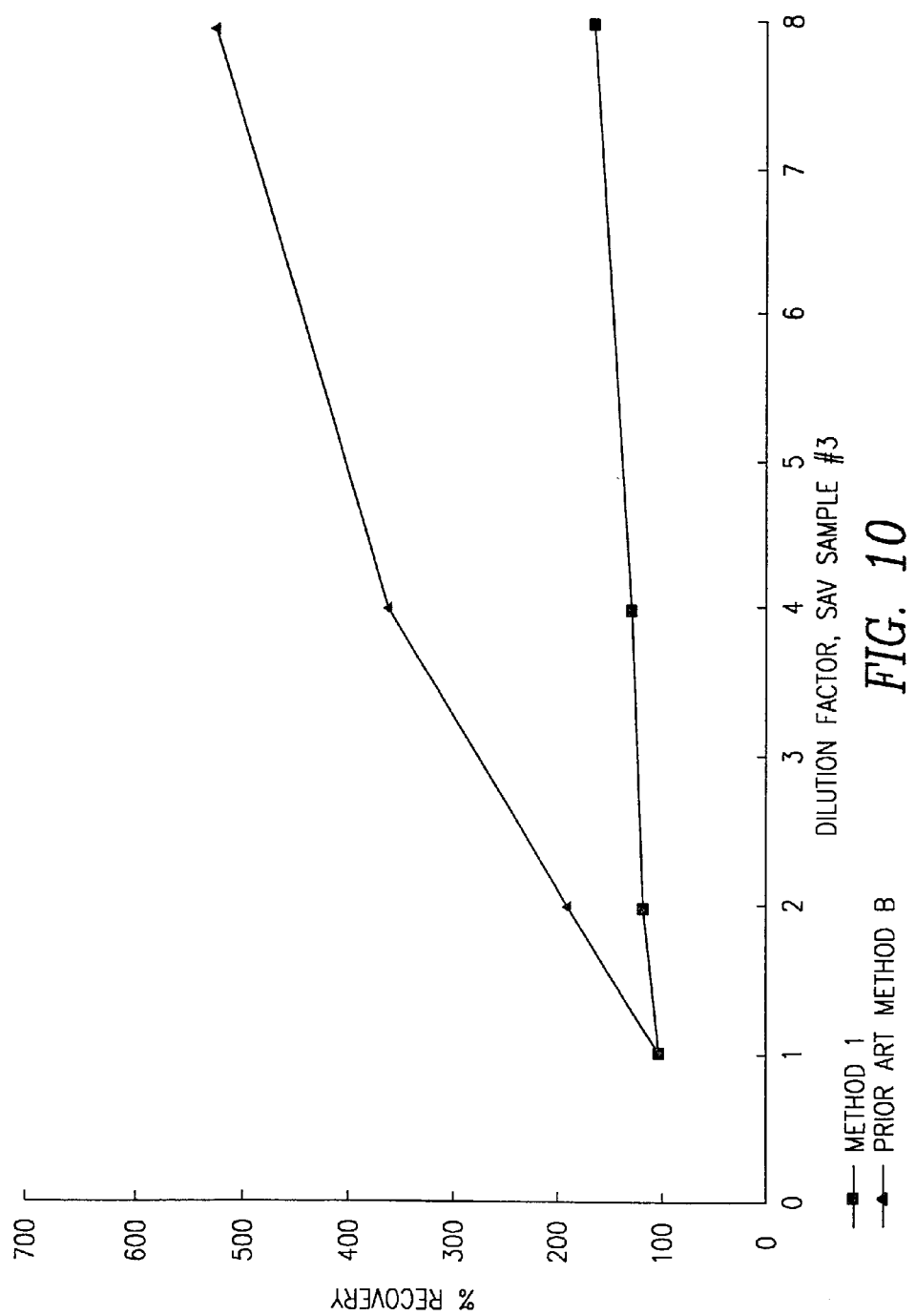
Figure 11:
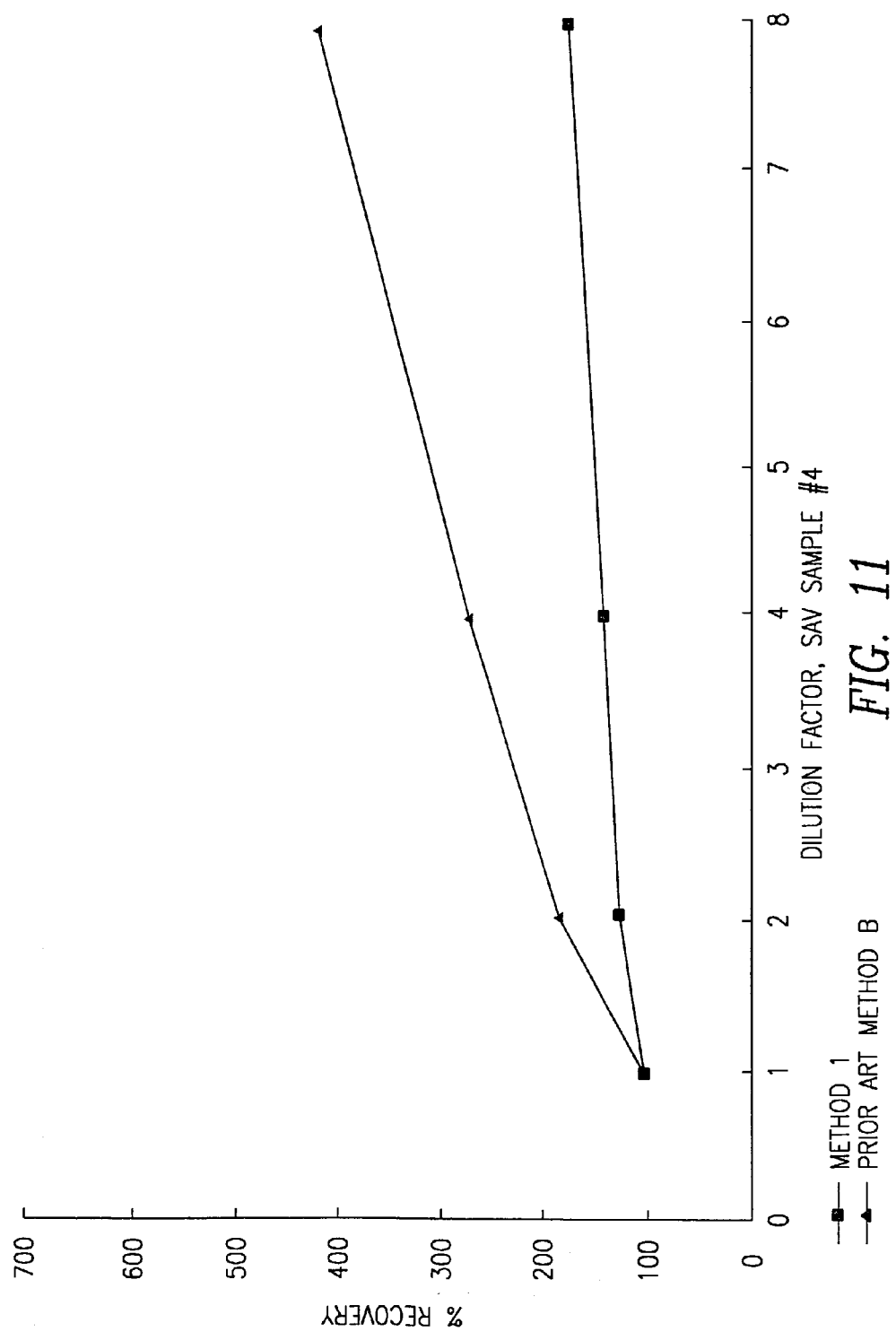
Figure 12:
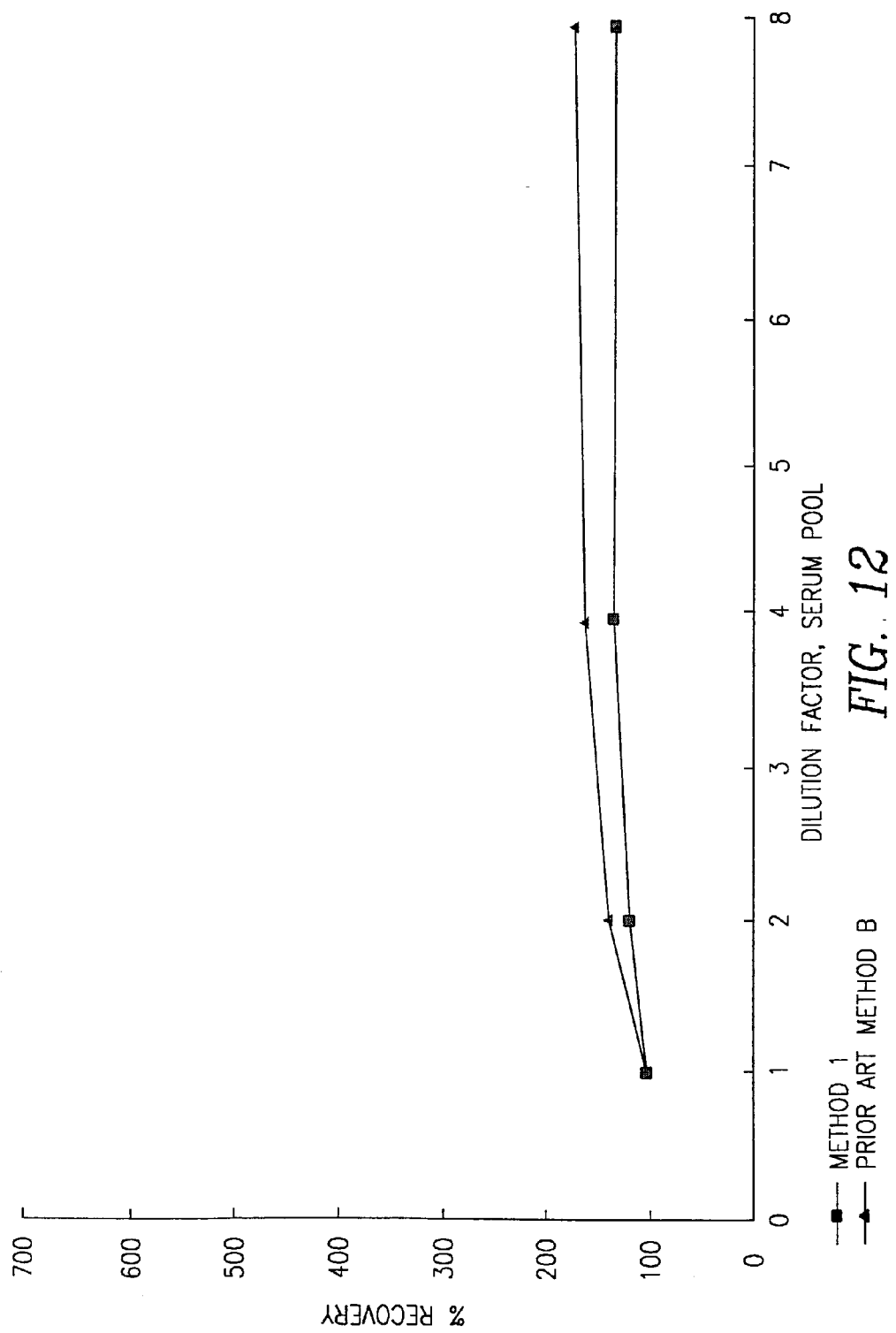

The results shown in FIG. 7 are expressed as % recovery calculated as the response obtained with rabbit antibody in the sample relative to the control. Responses were given in Signal/Background. Recoveries less than 100% indicate that addition of competing antibody reduces the response while recoveries higher than 100% indicate that addition of competing antibody increases the response.

It can be concluded that Method 1 have less interference with competing antibodies from other classes than the simultaneous method. While addition of competing antibodies results in a significant positive interference in Submethod 1, especially with high amounts of interfering antibodies, interference seems to be eliminated completely in Method 1.

Example 3

Dilution Curves with Samples from Patients Undergoing Specific Allergy Vaccination (SAV)

Determination of specific IgE against *Alternaria alternata* (mould) allergen was performed by Prior Art Method B and Method 1 as described in Example 1 except that biotinylated *Alternaria alternata* allergen was used instead of biotinylated *Betula verrucosa* allergen. The working dilution of biotinylated *Alternaria alternata* allergen was 1:400 in both the Prior Art Method and Method 1.

Sera from four patients undergoing Specific Allergy Vaccination (SAV) were serially diluted by a factor two to give four samples prior to analysis in each of the two different methods. As a reference sample, a serum pool of 5 *Alternaria alternata* sensitive patients was used.

FIG. 8-12 show results for samples from the four SAV patients and for the reference sample. The results shown in FIG. 8-12 are the responses obtained with the different diluted sera relative to the expected responses. % Recovery is calculated as (Dilution factor)*(Observed response)/(Response of undiluted sample). Responses were given in Signal/Background. Recoveries less than 100% indicate that the responses of the diluted sera are lower than expected while recoveries higher than 100% indicate that the responses are higher than expected. Recoveries higher than 100% therefore indicate that the response obtained with the undiluted sample is an underestimate of the true value.

It appears from FIGS. 8–12 that for the SAV samples the Prior Art Method underestimate the true value of the undiluted SAV samples while Method 1 result in much more correct estimates. For a serum pool of patients not subjected to SAV both methods perform satisfactorily by giving much more accurate values.

It can be concluded that Method 1 containing 2 washing steps, can much more reliably estimate the amount of allergen specific IgE in serum samples from patients subjected to SAV than the Prior Art Method B.

Example 4

Monitoring of Immune Response During House Dust Mite SAV

Determination of specific IgE against *Dermatophagoides pteronyssinus* (House dust mite) allergen was performed by Prior Art Method B and Method 1 as described in Example 1 except that biotinylated *Dermatophagoides pteronyssinus* allergen was used instead of biotinylated *Betula verrucosa* allergen. The working dilution of biotinylated *Dermatophagoides pteronyssinus* allergen was 1:250 in both Prior Art Method B and Method 1.

Figure 13:
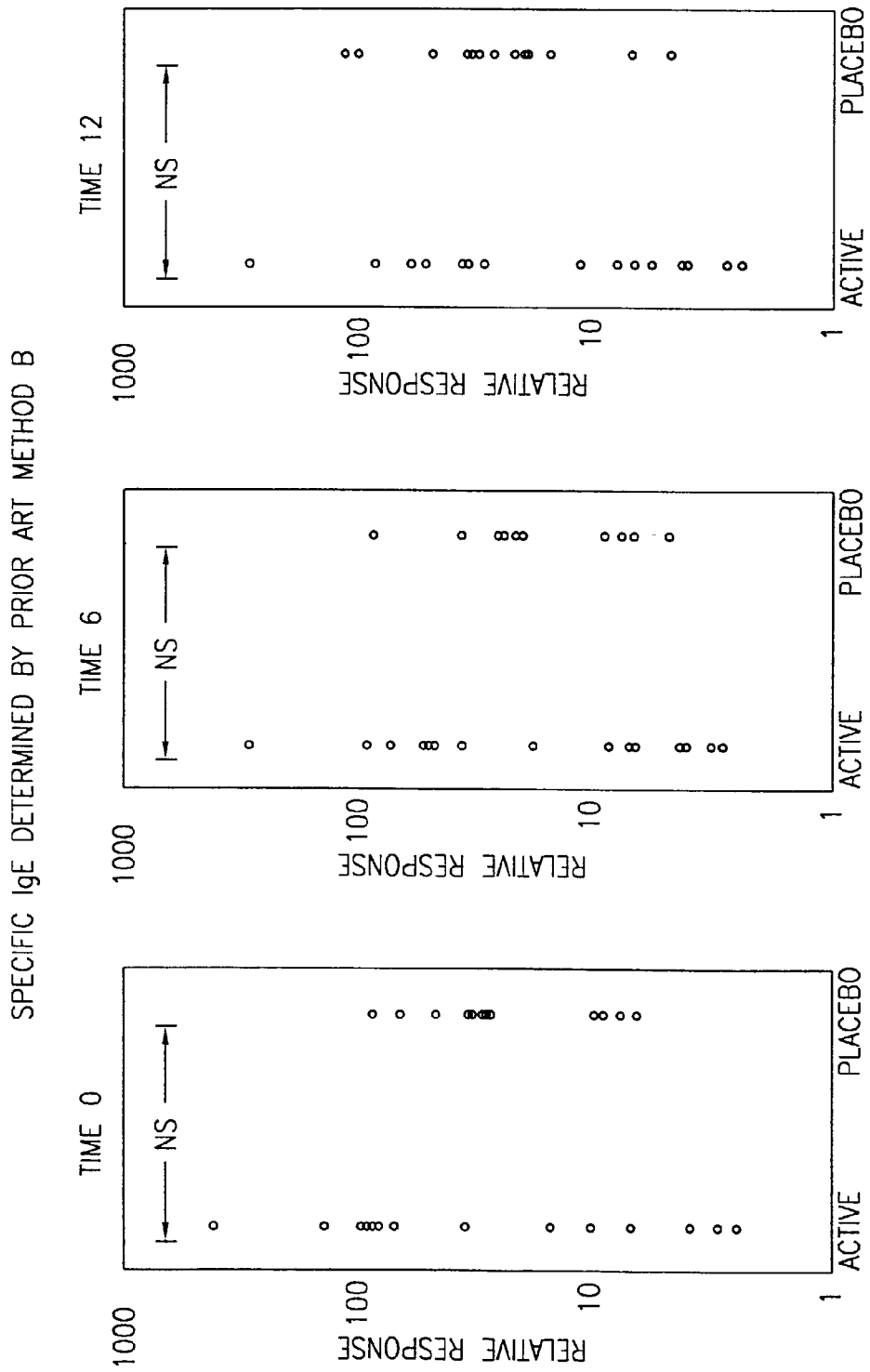
FIG. 13-14 show the relative response for patients subjected to Specific Allergy Vaccination and placebo treatment at 0, 6 and 12 months for Prior Art Method B and Method 1, respectively.
Figure 14:
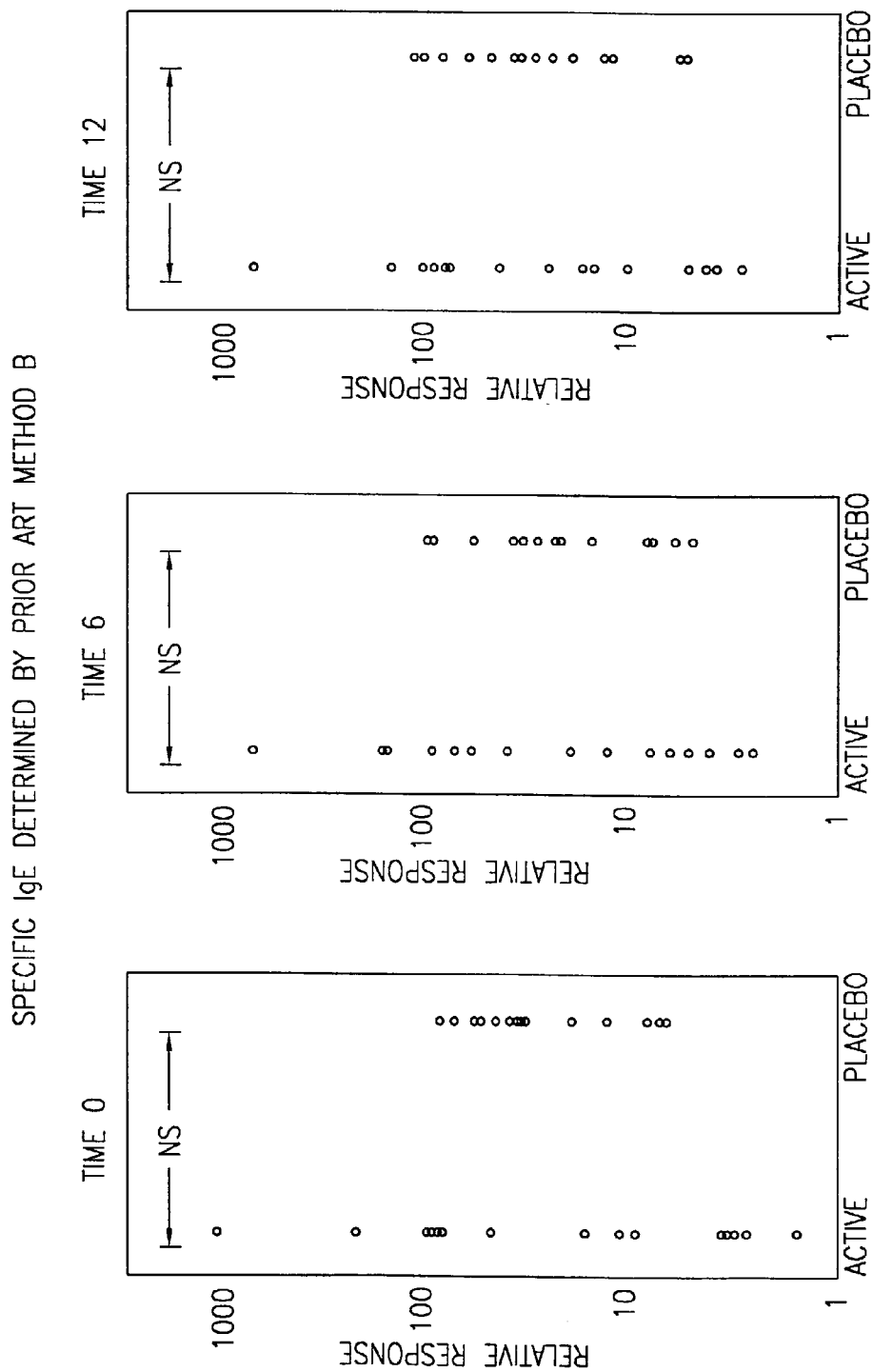
Figure 15:
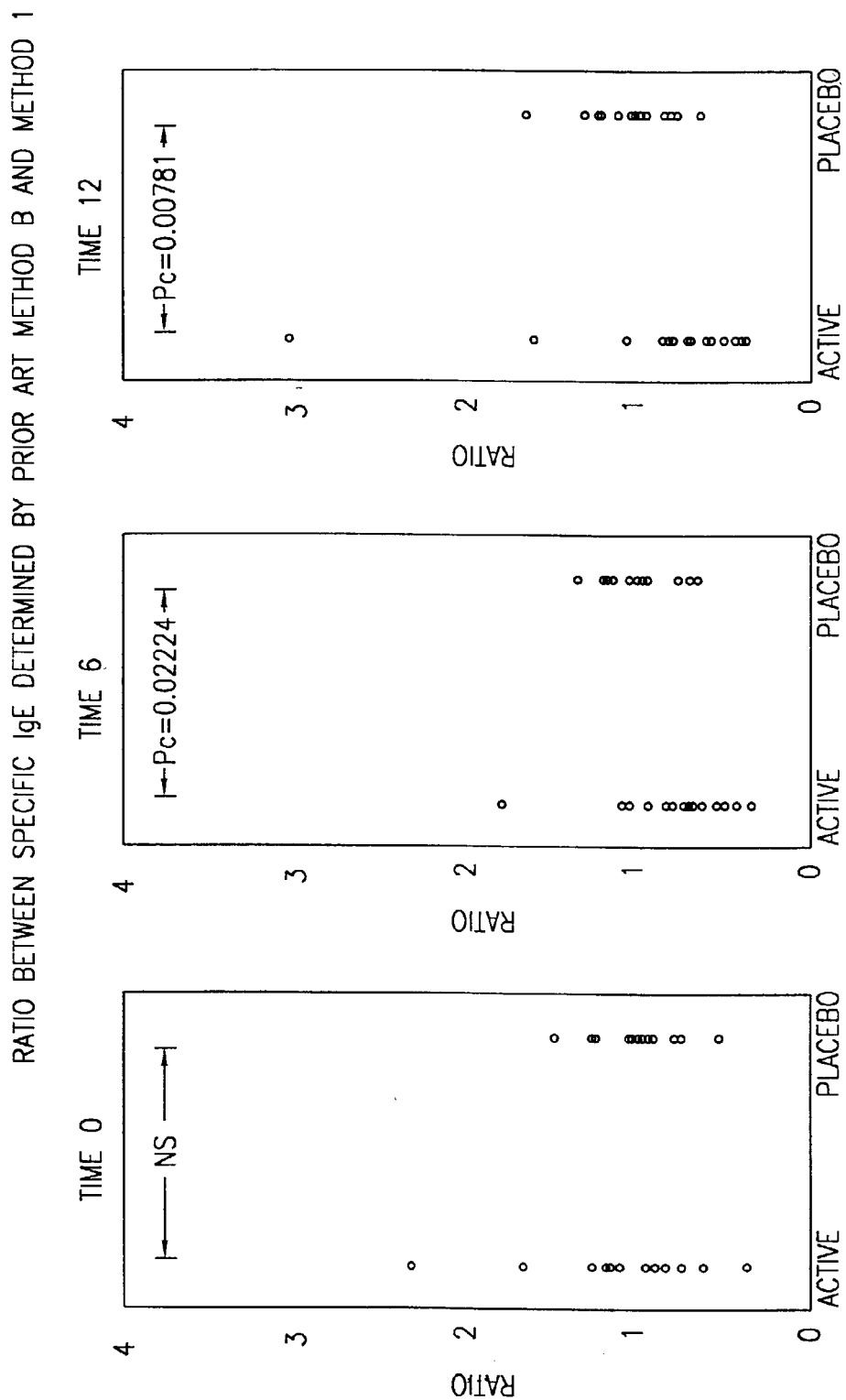
FIG. 15 show the ratio of responses obtained with Prior Art Method B to responses obtained with Method 1.

Serum samples were obtained from patients involved in a clinical study. A total of 30 patients were given either placebo treatment (N=14) or SAV with a 1:1 mixture of *Dermatophagoides pteronyssinus* and *Dermatophagoides farinae* allergen (Alutard, ALK-ABELLÓ A/S, Hrsholm, Denmark) (N=16). Samples were drawn prior to treatment (t=0), after 6 months of treatment (t=6) and after 12 months of treatment (t=12) and all samples were analysed by the two different methods. Results were obtained as Relative response=(Signal−Background)/(Signal$_{high}$−Background), where Signal$_{high}$ is the signal of a serum pool having a high content of the specific antibody to be detected. These results are shown in FIGS. 13–14. One additional set of data was generated by taking the ratio between results obtained in the Prior Art Method B and Method 1. These results are shown in FIG. 15.

Conclusion:

Neither of the methods (Prior Art Method B or Method 1) used to determine serum specific IgE are capable of discriminating active and placebo treatment groups during SAV (FIGS. 13–14). However, the ratio of the results obtained from the Prior Art Method and the method of the invention (Ratio=IgE(Prior Art Method B)$_t$/IgE(Method 1)$_t$) surprisingly discriminates active and placebo treatment groups 6 and 12 months after initiation of SAV (FIG. 15). Further, it is likely that a ratio cut-off value of approximately 1 may predict if the individual patient belonged to the placebo or active treatment group (FIG. 17, t=12) i.e. a SAV efficacy parameter.

Statistics:

Statistical analyses were performed by non-parametric tests (Mann-Whitney U-test). All two-sided stochastic probabilities less than 0.05 were considered significant. NS signifies non-significant, otherwise the actual probabilities are stated in the Figures.

Example 5

Monitoring of Immune Response During House Dust Mite SAV

Determination of specific IgE antibodies against *Dermatophagoides pteronyssinus* (House dust mite) allergen was performed by two different methods using the reagents described above in the working dilutions defined in each method. The two methods used were Prior Art Method A (FIG. 1a) and Method 1 according to the invention (FIG. 2a)

Prior Art Method A

This method is performed on a modified version of Ciba Corning ACS:180 Benchtop immunoassay Analyzer described in ref. 3. 25 µl of sample is dispensed by the sample probe into the cuvette and immidiately after this 100 µl of paramagnetic particles diluted 1:20 is dispensed by a fixed probe. After 8 minutes of incubation paramagnetic particles are magnetically separated and not washed. The paramagnetic particles are resuspended in 100 µl of washing buffer and 50 µl of biotinylated *Dermatophagoides pteronyssinus* allergen diluted 1:250 is added to the cuvette. After 10 minutes of incubation, 100 µl of lite reagent diluted 1:5000 is dispensed with a fixed probe and after additional 8 minutes of incubation the paramagnetic particles are magnetically separated and washed 3 times with 1 ml of washing buffer. After completion of the wash cycle the paramagnetic particles are resuspended in 300 µl 0.5 g/l $H_2O_2$ in 0.1 M $HNO_3$. The cuvette enters the luminometer chamber and in front of the photomultiplier 300 µl 25 mM NaOH solution is added and the photons of light emitted are measured and quantitated and expressed as relative light units (RLU). The amount of RLU is proportional to the amount of IgE in the sample. Results were expressed as RLU experiment/RLU background, where RLU background was the chemiluminescent reaction in the absence of IgE.

Method 1

This method is performed on a modified version of Ciba Corning ACS:180 Benchtop Immunoassay Analyzer described in ref. 2. 25 µl of sample is dispensed by the sample probe into the cuvette and immidiately after this 100 µl of paramagnetic particles diluted 1:20 is dispensed by a fixed probe. After 8 minutes of incubation paramagnetic particles are magnetically separated and washed once with 1 ml of washing buffer.

The paramagnetic particles are resuspended in 100 µl of washing buffer and 50 µl of biotinylated *Dermatophagoides pteronyssinus* allergen diluted 1:250 is added to the cuvette. After 10 minutes of incubation, 100 µl of lite reagent diluted 1:5000 is dispensed with a fixed probe and after additional 8 minutes of incubation the paramagnetic particles are magnetically separated and washed 3 times with 1 ml of washing buffer. After completion of the wash cycle the paramagnetic particles are resuspended in 300 µl 0.5 g/l $H_2O_2$ in 0.1 M $HNO_3$. The cuvette enters the luminometer chamber and in front of the photomultiplier 300 µl 25 mM NaOH solution is added and the photons of light emitted are measured and quantitated and expressed as relative light units (RLU). The amount of RLU is proportional to the amount of IgE in the sample. Results were expressed as RLU experiment/RLU background, where RLU background was the chemiluminescent reaction in the absence of IgE.

The present experimental work involve a total of 28 patients. 13 patients were not given any treatment, 7 patients were subjected to SAV treatment at a dosage level 100, and 8 patients were subjected to SAV treatment at a dosage of 300. The SAV treatment consisted in administering to the patient dosages of *Dermatophagoides pteronyssinus* (House dust mite) allergen by subcutaneous injections initially during an up-dosing period of 21 weeks with weekly injections, and subsequently during a two-year period with dosages of 100 or 300 SQ-units administered every 6–8 weeks.

The study uses an effect parameter based upon skin prick test (SPT) and broncial provocation test (BPT). The clinical effect parameter utilised here has been obtained as follows: The relative skin indexes (SI(time=x)–SI(time=0)) were used to cluster the patients in two groups (effect=decrease in skin sensitivity and no effect=unchanged skin sensitivity). Likewise the relative provocation test (logBPT(Time=x)–logBPT(time=0)) were used to cluster the patients in two groups (effect=decreased broncial sensitivity and no effect=unchanged broncial sensitivity). The two measures were combined into one clinical effect parameter: clinical effect=effect in both measures, no clinical effect=no effect in both measures and doubtful clinical effect=effect in one of the measures and no effect in the other measure.

Figure 16:
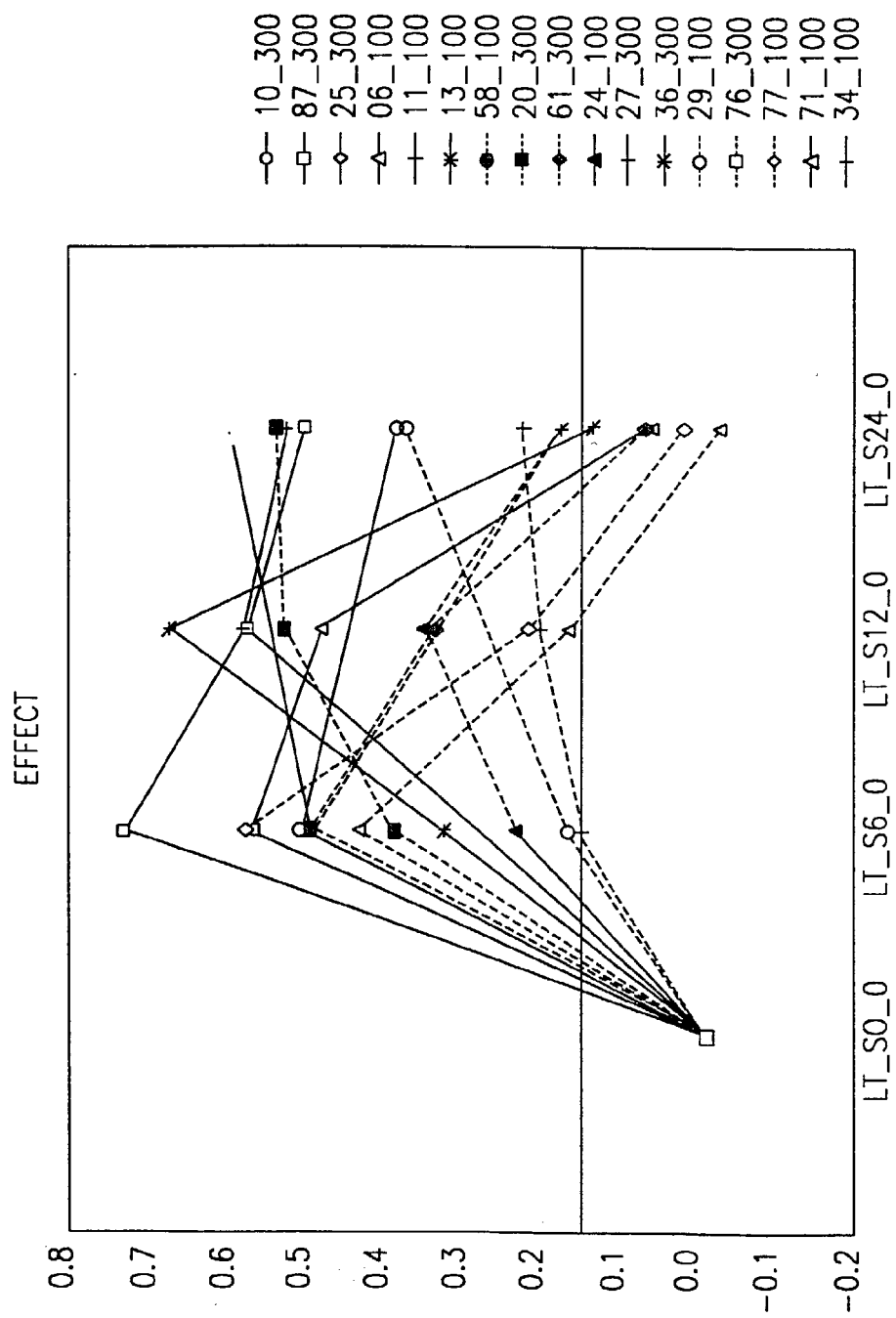
FIG. 16-18 show the relative IgE level at times 0, 6, 12 and 24 months for the three clinical effect groups Effect, No Effect and Doubtful, respectively.
Figure 17:
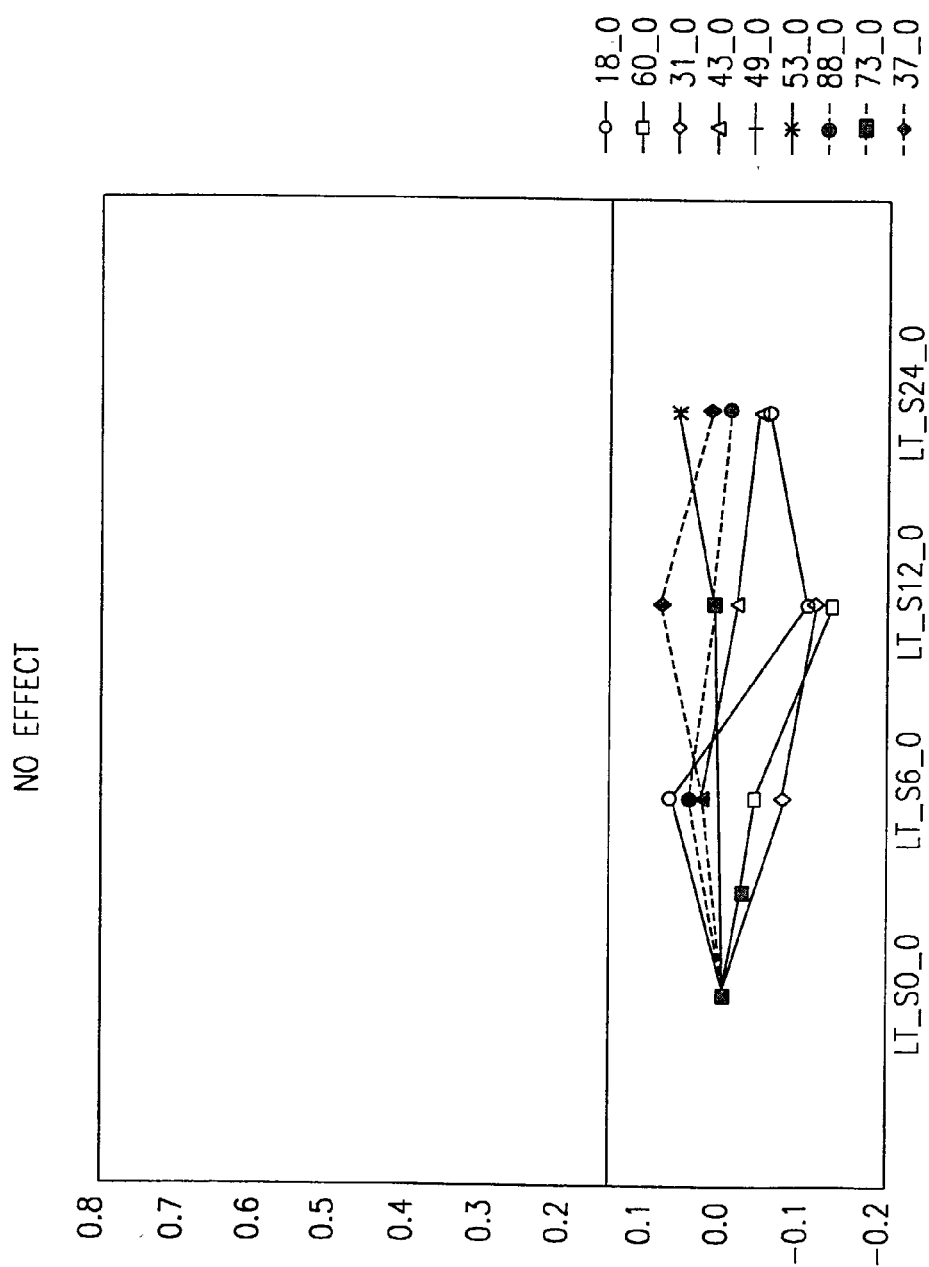
Figure 18:
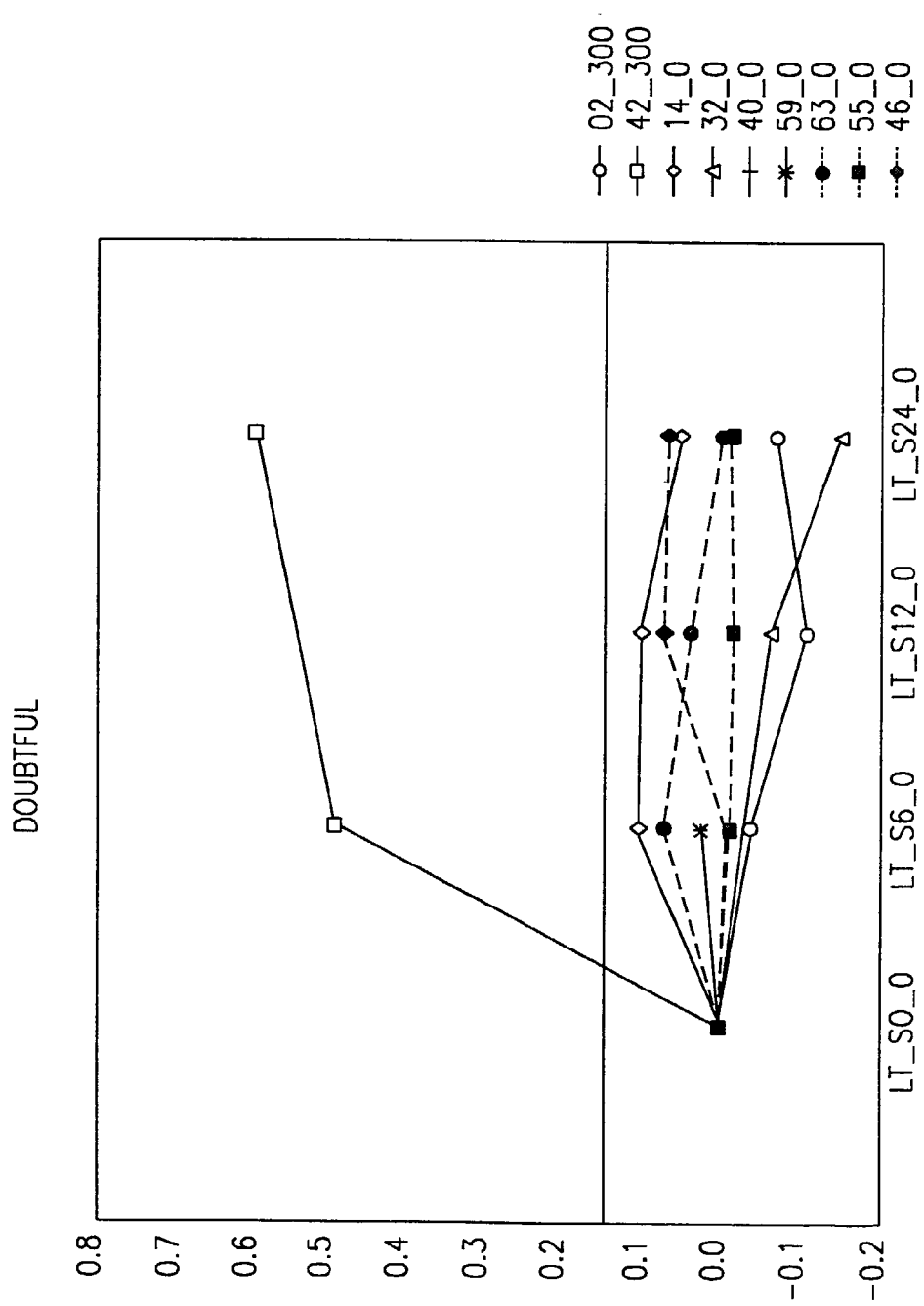

FIGS. 16–18 show the relative IgE level at times 0 (LT_S0_0), 6 (LT_S6_0), 12 (LT_S12_0) and 24 (LT_S24_0) months for the three clinical effect groups Effect, No Effect and Doubtful. Time=0 is the pretreatment value. The curve indications having the format nn__iii signifies patient identification number (nn) and type of treatment (iii), wherein iii=0 means no treatment and iii=100 or 300 means treatment at dosage level 100 and 300, respectively. The line at 0.14 is an arbitrary cut off value. The relative IgE level is defined as follows:

log(Response (Method 1)/Response(Prior Art Method A))$_{t=x}$–log(Response(Method 1)/Response (Prior Art Method A))$_{t=0}$, where t=time, x=0, 6, 12 or 24 months and Response=Signal/Background.

As will appear from FIG. 16, the response of Method 1 is higher than the response of Prior Art Method A for all of the patients that show a clinical effect, which means that a non IgE competing antibody response capable of reacting efficiently with the allergen has been initiated. It appears from FIG. 17 that none of the patients in the clinical no effect group develop a competing antibody response. Finally, it appears from FIG. 18 that one patient in the clinical doubtful group seem to develop a positive competing antibody response which are detected by only skin prick test. The test discriminates between treated and untreated patients since no patients from the control group (nn__0) is judged as if they raised a competing antibody response.

Conclusion

The ratio of IgE measured in the absence and presence of competing substances in the serum sample, i.e. measured by Method 1 and Prior Art Method A, respectively, seems to predict the effect of SAV. Furthermore, the in vitro measured effect is observable early in the treatment schedule. Although it is probable that the competing agent is an non IgE antibody—any serum substance reacting specifically with the allergens would be expected to behave similarly.

Example 6

Biotinylated Der p:

Der p 1 contains only one lysyl residue and the NH2-terminal aminoacid which are available for biotinylation. If one biotinylated a crude Der p extract using the "normal" labeling reagents (they target NH2-groups) the resulting labeled Der p extract tend to have biased sensitivity towards Der p 2 and other allergens.

A more balanced Der p reagent can be obtained as follows: crude Der p extract was biotinylated as described and a preparation of biotinylated Der p 1, labeled using biotin reagents capable of derivatizing tyrosine and histidine residues, was added. The resulting mixture was used in the following assays.

Biotinylation of Der p 1:

Der p 1 (ALK-Abelló A/S, Hrsholm, Denmark) was biotinylated with p-Diazobenzoyl Biocytin which was prepared from the stable precursor p-Aminobenzoyl Biocytin (Pierce, USA) according to the manufacturers instructions. The resulting solution of p-Diazobenzoyl Biocytin had a theoretical concentration of 1.82 mg/ml (equivalent to 3.38 mM), assuming 100% efficiency of conversion from p-Aminobenzoyl Biocytin to p-Diazobenzoyl Biocytin. Der p 1 was biotinylated in a molar ratio of 17:1, assuming a molecular weight of Der p 1 of 25 kDa, by adding 343 µl of p-Diazobenzoyl Biocytin solution to 1 ml of 1.74 mg/ml Der p 1 in 0.1 M $NaHCO_3$, pH 8.5. The subsequent steps in the process was as previously described for the biotinylation with Biotin-XX-NHS ester.

Instrumentation:

The samples were analyzed using an ADVIA Centaur analyzer (Bayer Diagnostics). The amount of Der p specific IgE in each sample were determined utilizing two protocols: a two step method (T) involving washing procedures which remove interfering substances (e.g. non IgE antibodies) before biotinylated allergens are added and a simultaneous protocol (S) which allow interfering substances (e.g. non IgE antibodies) to be present when the biotinylated allergens are added. Method T and Method S correspond to Method 1 and Prior Art Method A described in Example 5, except that the allergen was biotinylated as described above.

Materials and Methods:

Biotinylated allergen reagent was made by making a 1:250 dilution of biotinylated Der p 1 and mixing 1 part of this reagent with 4 parts of normal Der p reagent prepared and diluted as previously described.

Serum samples from (n=48) Der p allergic patients receiving SAV with Der p were obtained at 0, 0.5, 1, 2, 3, 6, 9, 12, 18 and 24 month after initiation of SAV. The patients were allocated in four treatment groups: controls (N=15), dose_10 (N=12), dose_100 (N=9) and dose _300 (N=11) and treated with Der p Alutard for 24 month with the dose indicated.

The clinical parameters SPT (Skin Prick Test), BPT (Bronchial Provocation Test) and CPT (Conjunctival Provocation Test) were measured before during and after SAV and a efficacy measure was constructed from the cluster analyzed clinical parameters. SAV was judged effective if two or three parameters was positive and noneffective if one or none of the parameters was positive.

IgE was measured in the serum samples according to the two protocols (T and S) and a baseline corrected in vitro efficacy parameter was calculated according to: $LN(Ti/Si)-LN(T0/S0)$ where i is the time (>0<=24) and 0 is the pretreatment values.

Figure 19:
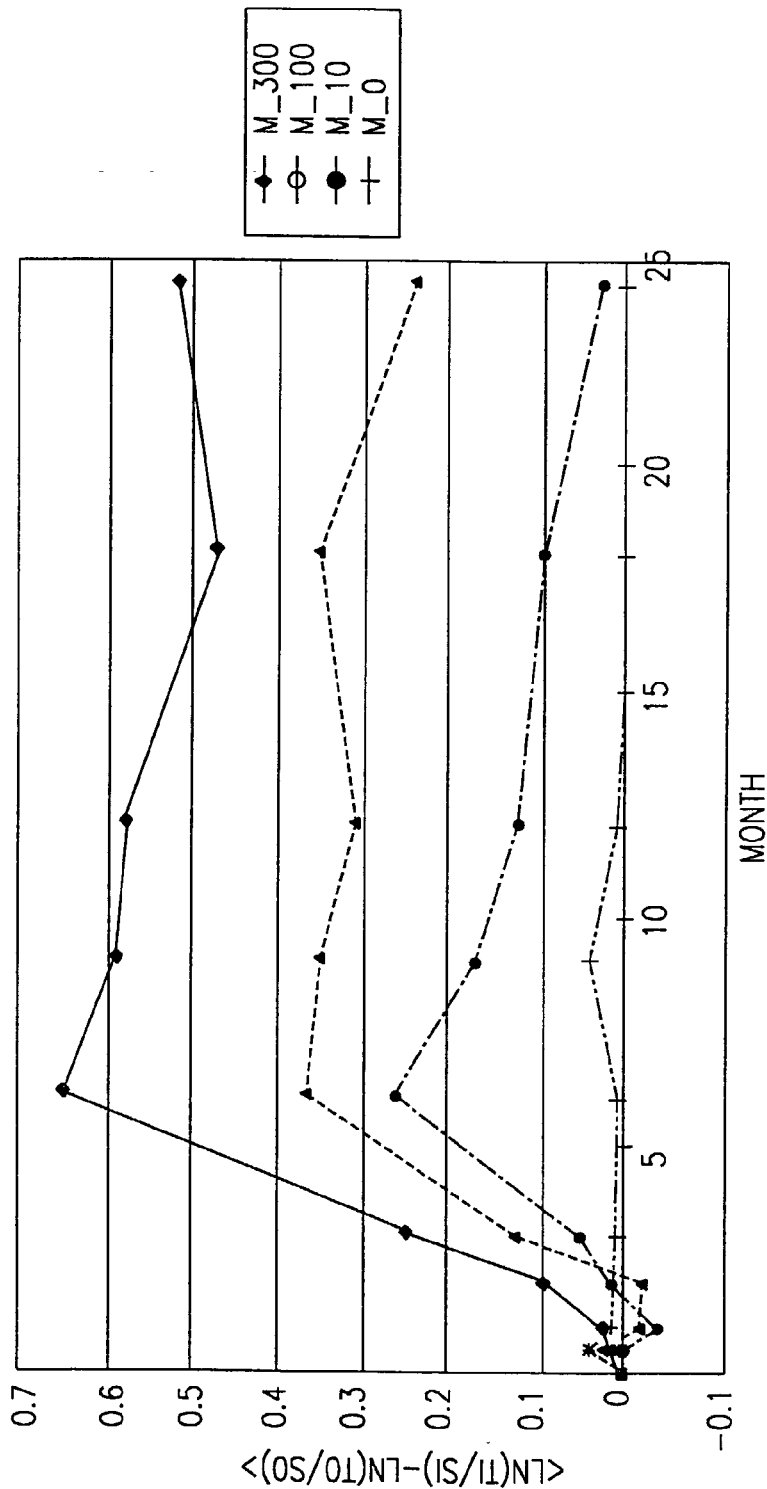
FIG. 19 shows the ratio of responses obtained with Method 1 to responses obtained with Prior Art Method B as a function of time for various SAV treatment doses.
Figure 20:
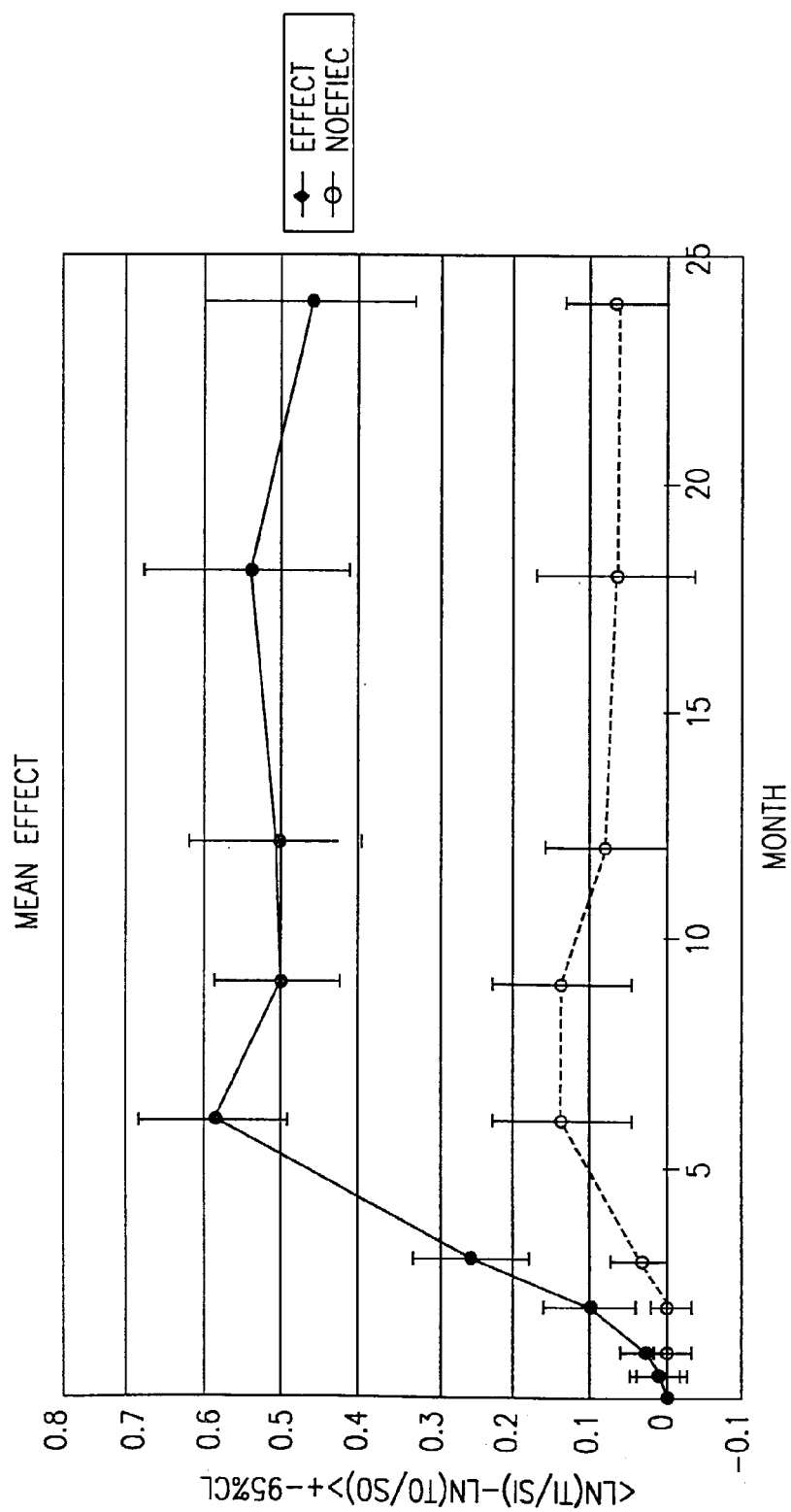
FIG. 20 shows the ratio of mean responses obtained with Method 1 to responses obtained with Prior Art Method 3 as a function of time for patients with clinical effect and patients without clinical effect, respectively.
Figure 21:
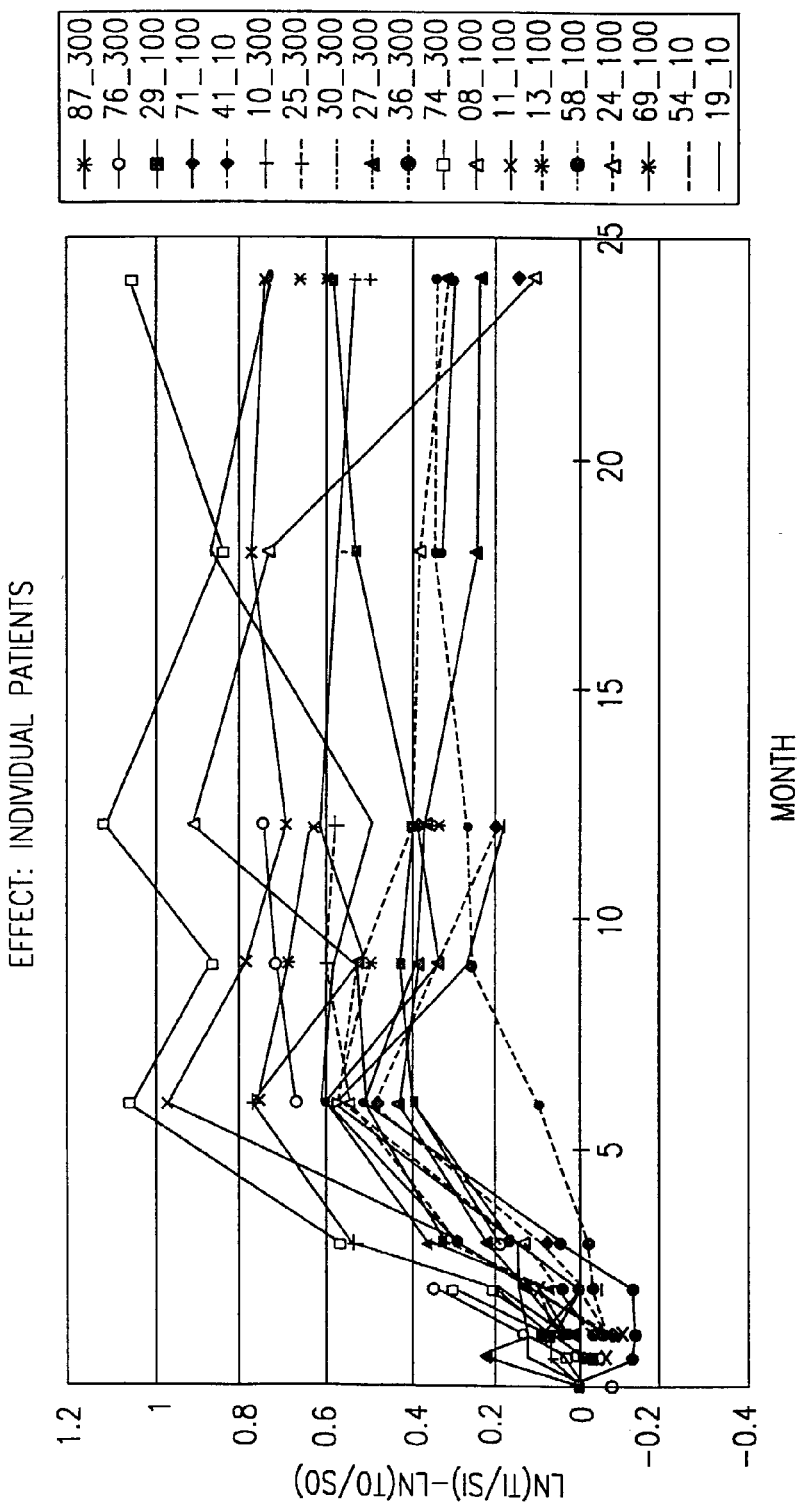
FIG. 21 shows the ratio of responses obtained with Method 1 to responses obtained with Prior Art Method B as a function of time for individual patients with clinical effect.
Figure 22:
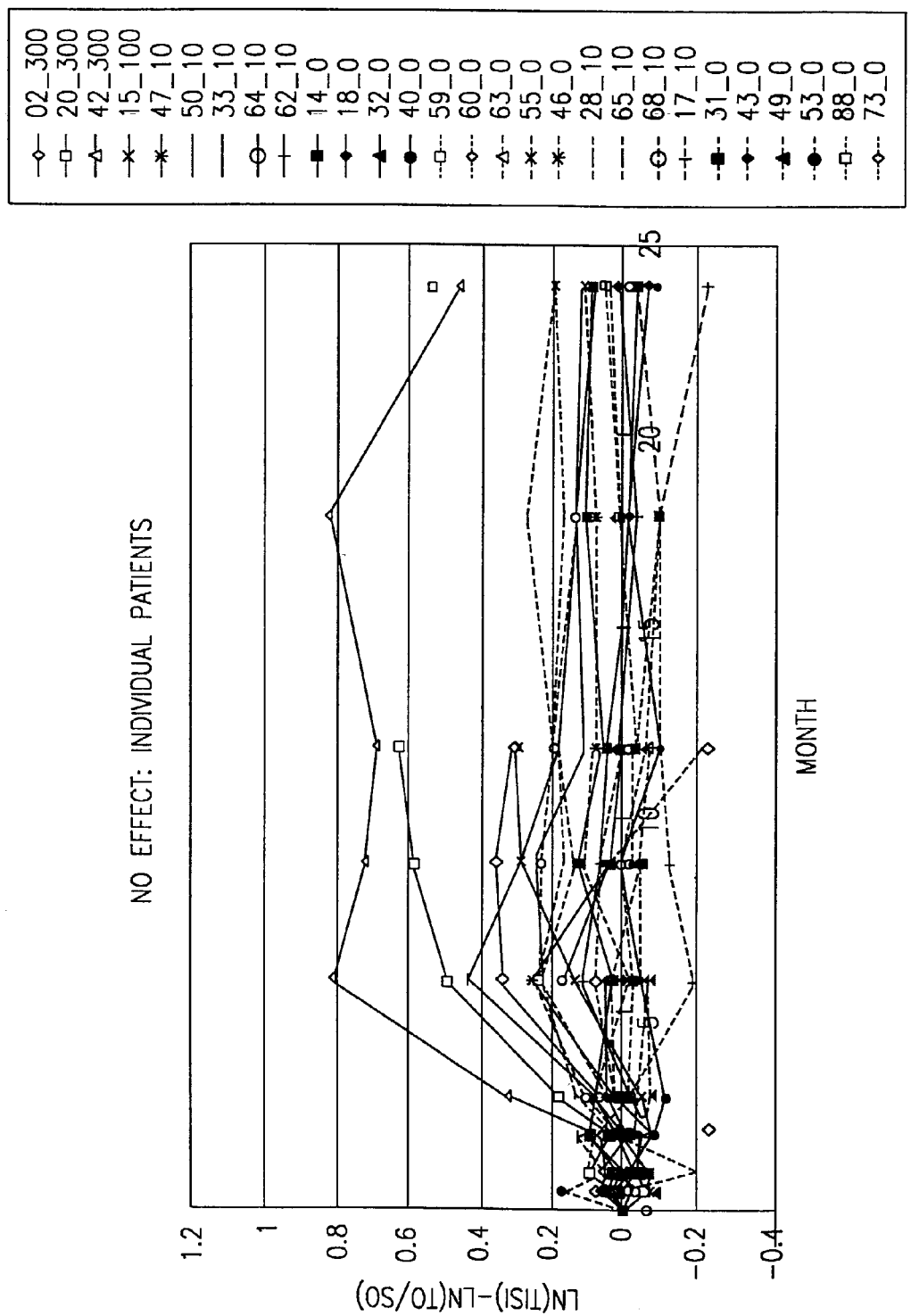
FIG. 22 shows the ratio of responses obtained with Method 1 to responses obtained with Prior Art Method B as a function of time for individual patients with no effect.

Results:

There is a clear dose response relationship between $LN(Ti/Si)-LN(T0/S0)$ and the dose given (FIG. 19; Dose-response relation of the effect parameter) indicating that the parameter measures a dose dependent immunological change in the patients. FIG. 20 (Mean effect parameter) illustrates the mean values obtained for the in vitro efficacy parameter for the patients with and without clinical effect and the in vitro parameter is shown for the individual patients in FIG. 21 (Effect: individual patients) and FIG. 22 (No effect: individual patients). All the patients with a positive clinical development show an increase of the in vitro parameter above the range of the control group from time 6 to 24 month and all these patients were receiving an active Der p SAV. Four patients (14%) with no apparent clinical effect are judged to have an effect by the in vitro effect parameter.

Conclusion:

The in vitro effect parameter seems to correlate well with the clinical assessment of the patient status, and the in vitro parameter is predictive of the outcome of SAV after 6 month of SAV whereas the clinical effects normally are obvious after 12 or 24 month.

REFERENCES

1) Ian Weeks, Iraj Beheshti, Frank McCapra, Anthony K. Campbell and J. Stuart Woodhead, *Clinical Chemistry,* 1983, 29, 1474–1479 (1983).
2) J. Boland, G. Carey, E. Krodel and M. Kwiatkowski, *Clinical Chemistry,* 1990, 36, 1598–1602.

What is claimed is:

1. A method of evaluating and/or predicting the effect of a Specific Allergy Vaccination treatment comprising the steps of:
   (h') determining the content of an antibody in a liquid sample using the following assay;
   (a') providing a mixture of a liquid phase and a three-component solid phase complex composed of (i) the antibody of the sample, (ii) a reactant antibody directed against the sample antibody, the reactant antibody being bound to a solid particle, and (iii) a ligand in the form of an antigen, an antibody or a hapten, where component (i) binds to components (ii) and (iii),
   (b') separating the three-component solid phase complex from the liquid phase,
   (c') washing the separated three-component solid phase complex to remove non-complex bound compounds,
   (d') adding to the three-component solid phase complex a solution of (iv) a label compound to form a four-component complex, where component (iv) binds to component (i), (ii) or (iii),
   (e') separating the four-component solid phase complex from the solution,
   (f') washing the separated four-component solid phase complex to remove non-complex bound label compound (iv),
   (g') performing a detection and/or measurement of the washed labeled four-component complex,
   (i') determining the content of the said antibody using the following assay;
      (ia') providing a mixture of a liquid phase and a four-component solid phase complex composed of (i) the antibody of the sample, (ii) a reactant antibody directed against the sample antibody, the reactant antibody being bound to a solid particle, (iii) a ligand in the form of an antigen, an antibody or a hapten, and (iv) a label compound, to form a four-component solid phase complex, where component (i) binds to components (ii) and (iii), and where component (iv) binds to component (i), (ii) or (iii),
      (ib') separating the four-component solid phase complex from the liquid phase,
      (ic') washing the separated four-component solid phase to remove non-complex bound compounds, and
      (id') performing a detection and/or measurement of the washed labeled four-component complex.
   (j') comparing the detection and/or measurements obtained in step (h') and step (i') and using the comparison to evaluate and/or predict the effect of the Specific Allergy Vaccination treatment, wherein an effect is obtained if the detection and/or measurement in step (i') is less than the detection and/or measurement in step (h').

2. The method according to claim 1, wherein step (ia') is carried out by mixing components (i) and (ii), then adding component (iii), and finally adding component (iv).

3. The method according to claim 1, wherein step (ia'), is carried out by mixing components (i), (ii) and (iii), and then adding component (iv).

4. The method according to claim 1, wherein the comparison of step (j') is carried out by calculating the ratio of the measurements obtained in the two said steps.

5. The method according to claim 1, wherein the comparison of step (j') is carried out in at least one point during the treatment, and that any temporal change, which may be observed, is used as a basis for evaluating and/or predicting the effect of the treatment.

6. The method according to claim 1, wherein in step (a') and in step (ia') the ligand is bound to biotin or a functional derivative thereof, and wherein in step (d') and in step (ia') the label compound is a chemiluminescent compound covalently bound to avidin, streptavidin or a functional derivative thereof, and wherein step (g') and in step (id') the detection and/or measurement step comprises initiating a chemiluminescent reaction in the washed four-component solid phase complex and detecting and/or measuring the resulting chemiluminescence.

7. The method according to claim 6, wherein in step (a') and in step (ia') the solid particle is a solid paramagnetic particle, and wherein step (b'), step (a') and step (ib') comprise magnetically separating the solid phase complex from the liquid phase.

8. The method according to claim 6 wherein step (ia') is carried out by mixing components (i) and (ii), then adding component (iii), and finally adding component (iv).

9. The method according to claim 7 wherein step (ia') is carried out by mixing components (i) and (ii), then adding component (iii), and finally adding component (iv).

10. The method according to claim 6, wherein step (ia'), is carried out by mixing components (i), (ii) and (iii), and then adding component (iv).

11. The method according to claim 7 wherein step (ia'), is carried out by mixing components (i), (ii) and (iii), and then adding component (iv).

12. The method according to claim 6 wherein the comparison of step (j') is carried out by calculating the ratio of the measurements obtained in the two said steps.

13. The method according to claim 7 wherein the comparison of step (j') is carried out by calculating the ratio of the measurements obtained in the two said steps.

14. The method according to claim 6 wherein the comparison of step (j') is carried out in at least one point during the treatment, and that any temporal change, which may be observed, is used as a basis for evaluating and/or predicting the effect of the treatment.

15. The method according to claim 7 wherein the comparison of step (j') is carried out in at least one point during the treatment, and that any temporal change, which may be observed, is used as a basis for evaluating and/or predicting the effect of the treatment.

16. The method according to claim 6 wherein the sample antibody is IgE.

17. The method according to claim 7 wherein the sample antibody is IgE.

* * * * *

UNITED STATES PATENT AND TRADEMARK OFFICE
CERTIFICATE OF CORRECTION

PATENT NO. : 6,939,681 B1
DATED : September 6, 2005
INVENTOR(S) : Hans-Henrik Ipsen et al.

It is certified that error appears in the above-identified patent and that said Letters Patent is hereby corrected as shown below:

Column 17,
Line 29, please cancel "step (a')" and insert -- step (e') --.

Signed and Sealed this

Twenty-seventh Day of December, 2005

JON W. DUDAS
*Director of the United States Patent and Trademark Office*